(12) United States Patent
Gillies et al.

(10) Patent No.: US 7,517,526 B2
(45) Date of Patent: Apr. 14, 2009

(54) ENHANCEMENT OF ANTIBODY-CYTOKINE FUSION PROTEIN MEDIATED IMMUNE RESPONSES BY COMBINED TREATMENT WITH IMMUNOCYTOKINE UPTAKE ENHANCING AGENTS

(75) Inventors: Stephen D. Gillies, Carlisle, MA (US); Yan Lan, Belmont, MA (US); Sylvia Holden, Woburn, MA (US)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 09/896,909

(22) Filed: Jun. 29, 2001

(65) Prior Publication Data

US 2003/0049227 A1    Mar. 13, 2003

Related U.S. Application Data

(60) Provisional application No. 60/215,038, filed on Jun. 29, 2000.

(51) Int. Cl.
*A61K 39/395* (2006.01)
*C07K 14/52* (2006.01)

(52) U.S. Cl. ...................... 424/178.1; 530/402; 530/351
(58) Field of Classification Search ............. 530/382.3, 530/383, 388.85, 300, 350, 351; 424/134.1, 424/155.1
See application file for complete search history.

(56) References Cited

U.S. PATENT DOCUMENTS

| | | | |
|---|---|---|---|
| 4,196,265 A | 4/1980 | Koprowski et al. |
| 4,469,797 A | 9/1984 | Albarella |
| 4,676,980 A | 6/1987 | Segal et al. |
| 4,703,008 A | 10/1987 | Lin |
| 4,816,567 A | 3/1989 | Cabilly et al. |
| 4,946,778 A | 8/1990 | Ladner et al. |
| 4,975,369 A | 12/1990 | Beavers et al. |
| 5,019,368 A | 5/1991 | Epstein et al. |
| 5,073,627 A | 12/1991 | Curtis et al. |
| 5,082,658 A | 1/1992 | Palladino |
| 5,091,513 A | 2/1992 | Huston et al. |
| 5,114,711 A | 5/1992 | Bell et al. |
| 5,116,964 A | 5/1992 | Capon et al. |
| 5,199,942 A | 4/1993 | Gillis |
| 5,225,538 A | 7/1993 | Capon et al. |
| 5,225,539 A | 7/1993 | Winter |
| 5,258,498 A | 11/1993 | Huston et al. |
| 5,314,995 A | 5/1994 | Fell, Jr. et al. |
| 5,349,053 A | 9/1994 | Landolfi |
| 5,359,035 A | 10/1994 | Habermann |
| 5,399,346 A | 3/1995 | Anderson et al. |
| 5,428,130 A | 6/1995 | Capon et al. |
| 5,441,868 A | 8/1995 | Lin |
| 5,457,038 A | 10/1995 | Trinchieri et al. |
| 5,480,981 A | 1/1996 | Goodwin et al. |
| 5,514,582 A | 5/1996 | Capon et al. |
| 5,538,866 A | 7/1996 | Israeli et al. |
| 5,541,087 A | 7/1996 | Lo et al. |
| 5,543,297 A | 8/1996 | Cromlish et al. |
| 5,547,933 A | 8/1996 | Lin |
| 5,552,524 A | 9/1996 | Basinski et al. |
| 5,585,089 A | 12/1996 | Queen et al. |
| 5,601,819 A | 2/1997 | Wong et al. |
| 5,609,846 A | 3/1997 | Goldenberg |
| 5,614,184 A | 3/1997 | Sytkowski et al. |
| 5,618,698 A | 4/1997 | Lin |
| 5,624,821 A | 4/1997 | Winter et al. |
| 5,639,725 A | 6/1997 | O'Reilly et al. |
| 5,645,835 A | 7/1997 | Fell, Jr. et al. |
| 5,650,150 A * | 7/1997 | Gillies |
| 5,650,492 A | 7/1997 | Gately et al. |
| 5,667,776 A | 9/1997 | Zimmerman et al. |
| 5,679,543 A | 10/1997 | Lawlis |
| 5,688,679 A | 11/1997 | Powell |
| 5,691,309 A | 11/1997 | Basinski et al. |
| 5,709,859 A | 1/1998 | Aruffo et al. |
| 5,712,120 A | 1/1998 | Rodriguez et al. |
| 5,719,266 A | 2/1998 | DiMarchi et al. |
| 5,723,125 A | 3/1998 | Chang et al. |
| 5,726,044 A | 3/1998 | Lo et al. |
| 5,728,552 A | 3/1998 | Fujisawa et al. |
| 5,733,876 A | 3/1998 | O'Reilly et al. |
| 5,756,349 A | 5/1998 | Lin |
| 5,756,461 A | 5/1998 | Stephens |
| 5,759,551 A | 6/1998 | Ladd et al. |
| 5,770,195 A | 6/1998 | Hudziak et al. |
| 5,800,810 A | 9/1998 | Doyle et al. |
| 5,807,715 A | 9/1998 | Morrison et al. |
| 5,827,516 A | 10/1998 | Urban et al. |
| 5,827,703 A | 10/1998 | Debs et al. |
| 5,837,682 A | 11/1998 | Folkman et al. |
| 5,837,821 A | 11/1998 | Wu |
| 5,843,423 A | 12/1998 | Lyman et al. |
| 5,854,205 A | 12/1998 | O'Reilly et al. |
| 5,856,298 A | 1/1999 | Strickland |
| 5,858,347 A | 1/1999 | Bauer et al. |
| 5,885,795 A | 3/1999 | O'Reilly et al. |
| 5,886,178 A | 3/1999 | Allen et al. |
| 5,888,772 A | 3/1999 | Okasinski et al. |

(Continued)

FOREIGN PATENT DOCUMENTS

AU         21725/88        3/1989

(Continued)

OTHER PUBLICATIONS

Strom et al., Therapeutic Immunology Blackwell Science, chapter 36, pp. 451-456, 1996.*

(Continued)

*Primary Examiner*—Christopher H Yaen
(74) *Attorney, Agent, or Firm*—Goodwin Procter LLP

(57) ABSTRACT

Disclosed are methods and compositions for treating tumors. Disclosed methods and compositions enhance the uptake of immunocytokines into tumors, and are based on a combination of an immunocytokine with an immunocytokine uptake enhancing agent. Disclosed methods and compositions are particularly useful for reducing tumor size and metastasis in a mammal.

17 Claims, 12 Drawing Sheets

U.S. PATENT DOCUMENTS

| | | | |
|---|---|---|---|
| 5,888,773 A | 3/1999 | Jost et al. |
| 5,891,680 A | 4/1999 | Lieschke et al. |
| 5,908,626 A | 6/1999 | Chang et al. |
| 5,922,685 A | 7/1999 | Rakhmilevich et al. |
| 5,955,422 A | 9/1999 | Lin |
| 5,994,104 A | 11/1999 | Anderson et al. |
| 5,994,126 A | 11/1999 | Steinman et al. |
| 6,080,409 A | 6/2000 | Laus et al. |
| 6,086,875 A | 7/2000 | Blumberg et al. |
| 6,100,387 A | 8/2000 | Herrmann et al. |
| 6,169,070 B1 | 1/2001 | Chen et al. |
| 6,171,588 B1 | 1/2001 | Carron et al. |
| 6,231,536 B1 * | 5/2001 | Lentz |
| 6,277,375 B1 | 8/2001 | Ward |
| 6,281,010 B1 | 8/2001 | Gao et al. |
| 6,284,536 B1 | 9/2001 | Morrison et al. |
| 6,291,158 B1 | 9/2001 | Winter et al. |
| 6,335,176 B1 | 1/2002 | Inglese et al. |
| 6,340,742 B1 | 1/2002 | Burg et al. |
| 6,348,192 B1 | 2/2002 | Chan et al. |
| 6,406,689 B1 | 6/2002 | Falkenberg et al. |
| 6,444,792 B1 | 9/2002 | Gray et al. |
| 6,475,717 B1 | 11/2002 | Enssle et al. |
| 6,485,726 B1 | 11/2002 | Blumberg et al. |
| 6,500,641 B1 | 12/2002 | Chen et al. |
| 6,506,405 B1 * | 1/2003 | Desai et al. |
| 6,551,592 B2 | 4/2003 | Lindhofer et al. |
| 6,583,272 B1 | 6/2003 | Bailon |
| 6,586,398 B1 | 7/2003 | Kinstler et al. |
| 6,617,135 B1 | 9/2003 | Gillies et al. |
| 6,627,615 B1 | 9/2003 | Debs et al. |
| 6,646,113 B1 | 11/2003 | Dreyfuss et al. |
| 6,750,329 B1 | 6/2004 | Rosenblum et al. |
| 6,838,260 B2 | 1/2005 | Gillies et al. |
| 2001/0053539 A1 | 12/2001 | Lauffer et al. |
| 2002/0037558 A1 | 3/2002 | Lo et al. |
| 2002/0081664 A1 | 6/2002 | Lo et al. |
| 2002/0142374 A1 | 10/2002 | Gallo et al. |
| 2002/0146388 A1 | 10/2002 | Gillies |
| 2002/0147311 A1 | 10/2002 | Gillies et al. |
| 2002/0192222 A1 | 12/2002 | Blumberg et al. |
| 2002/0193570 A1 | 12/2002 | Gillies et al. |
| 2003/0003529 A1 | 1/2003 | Bayer |
| 2003/0012789 A1 | 1/2003 | Blumberg et al. |
| 2003/0044423 A1 | 3/2003 | Gillies et al. |
| 2003/0049227 A1 | 3/2003 | Gillies et al. |
| 2003/0105294 A1 | 6/2003 | Gillies et al. |
| 2003/0139365 A1 | 7/2003 | Lo et al. |
| 2003/0139575 A1 | 7/2003 | Gillies |
| 2003/0157054 A1 | 8/2003 | Gillies et al. |
| 2003/0166163 A1 | 9/2003 | Gillies |
| 2003/0166877 A1 | 9/2003 | Gillies et al. |
| 2004/0013640 A1 | 1/2004 | Zardi et al. |
| 2004/0033210 A1 | 2/2004 | Gillies |
| 2004/0043457 A1 | 3/2004 | Schumacher et al. |
| 2004/0053366 A1 | 3/2004 | Lo et al. |
| 2004/0072299 A1 | 4/2004 | Gillies et al. |
| 2004/0082039 A1 | 4/2004 | Gillies et al. |
| 2004/0180035 A1 | 9/2004 | Gillies et al. |
| 2004/0180386 A1 | 9/2004 | Carr et al. |
| 2004/0203100 A1 | 10/2004 | Gillies et al. |

FOREIGN PATENT DOCUMENTS

| | | |
|---|---|---|
| CN | 93100115.3 | 7/1993 |
| DE | 37 12985 | 11/1988 |
| EP | 0 158 198 | 10/1985 |
| EP | 0 211 769 | 2/1987 |
| EP | 0 237 019 | 9/1987 |
| EP | 0 256 714 | 2/1988 |
| EP | 0 294 703 | 12/1988 |
| EP | 0 308 936 | 3/1989 |
| EP | 0 314 317 | 5/1989 |
| EP | 0 318 554 | 6/1989 |
| EP | 0 319 012 | 6/1989 |
| EP | 0 326 120 | 8/1989 |
| EP | 0 350 230 | 1/1990 |
| EP | 0 375 562 | 6/1990 |
| EP | 0 396 387 | 11/1990 |
| EP | 0 439 095 | 7/1991 |
| EP | 0 511 747 | 11/1992 |
| EP | 0 519 596 A1 | 12/1992 |
| EP | 0 344 134 B1 | 1/1994 |
| EP | 0 601 043 | 6/1994 |
| EP | 0 640 619 A1 | 3/1995 |
| EP | 0 668 353 A1 | 8/1995 |
| EP | 0 699 755 A2 | 3/1996 |
| EP | 0 428 596 B1 | 4/1996 |
| EP | 0 706 799 | 4/1996 |
| EP | 0 790 309 | 8/1997 |
| EP | 0 433 827 B1 | 3/1998 |
| EP | 1 088 888 A1 | 4/2001 |
| GB | 2 188 638 | 10/1987 |
| GB | 2 292 382 | 2/1996 |
| JP | 63-267278 | 11/1988 |
| JP | 63-267296 | 11/1988 |
| WO | WO 86/01533 | 3/1986 |
| WO | WO 88/00052 | 1/1988 |
| WO | WO 88/09344 | 12/1988 |
| WO | WO 89/02922 | 4/1989 |
| WO | WO 89/09620 | 10/1989 |
| WO | WO 90/03801 | 4/1990 |
| WO | WO 91/00360 | 1/1991 |
| WO | WO 91/04329 | 4/1991 |
| WO | WO 91/08298 | 6/1991 |
| WO | WO 91/13166 | 9/1991 |
| WO | WO 91/14438 | 10/1991 |
| WO | WO 92/02240 | 2/1992 |
| WO | WO 92/08495 | 5/1992 |
| WO | WO 92/08801 | 5/1992 |
| WO | WO 92/10755 | 6/1992 |
| WO | WO 92/16562 | 10/1992 |
| WO | WO 93/03157 | 2/1993 |
| WO | WO 93/10229 | 5/1993 |
| WO | WO 94/24160 | 10/1994 |
| WO | WO 94/25055 | 11/1994 |
| WO | WO 94/25609 | 11/1994 |
| WO | WO 95/05468 | 2/1995 |
| WO | WO 95/21258 | 8/1995 |
| WO | WO 95/28427 | 10/1995 |
| WO | WO 95/31483 | 11/1995 |
| WO | WO 96/04388 | 2/1996 |
| WO | WO 96/05309 | 2/1996 |
| WO | WO 96/08570 | 3/1996 |
| WO | WO 96/18412 | 6/1996 |
| WO | WO 96/31526 | 10/1996 |
| WO | WO 96/40792 | 12/1996 |
| WO | WO 97/00317 | 1/1997 |
| WO | WO 97/00319 | 1/1997 |
| WO | WO 97/15666 | 5/1997 |
| WO | WO 97/20062 | 6/1997 |
| WO | WO 97/24137 | 7/1997 |
| WO | WO 97/24440 | 7/1997 |
| WO | WO 97/26335 | 7/1997 |
| WO | WO 97/30089 | 8/1997 |
| WO | WO 97/33617 | 9/1997 |
| WO | WO 97/33619 | 9/1997 |
| WO | WO 97/34631 | 9/1997 |
| WO | WO 97/43316 | 11/1997 |
| WO | WO 98/00127 | 1/1998 |
| WO | WO 98/06752 | 2/1998 |
| WO | WO 98/28427 | 7/1998 |
| WO | WO 98/30706 | 7/1998 |
| WO | WO 98/46257 | 10/1998 |

| | | |
|---|---|---|
| WO | WO 98/52976 | 11/1998 |
| WO | WO 98/59244 | 12/1998 |
| WO | WO 99/02709 | 1/1999 |
| WO | WO 99/03887 | 1/1999 |
| WO | WO 99/29732 | 6/1999 |
| WO | WO 99/43713 | 9/1999 |
| WO | WO 99/52562 | 10/1999 |
| WO | WO 99/53958 | 10/1999 |
| WO | WO 99/60128 | 11/1999 |
| WO | WO 99/62944 | 12/1999 |
| WO | WO 99/66054 | 12/1999 |
| WO | WO 00/01822 | 1/2000 |
| WO | WO 00/11033 | 3/2000 |
| WO | WO 00/24893 | 5/2000 |
| WO | WO 00/34317 | 6/2000 |
| WO | WO 00/40615 | 7/2000 |
| WO | WO 00/68376 | 11/2000 |
| WO | WO 00/69913 | 11/2000 |
| WO | WO 00/78334 | 12/2000 |
| WO | WO 01/07081 | 2/2001 |
| WO | WO 01/10912 | 2/2001 |
| WO | WO 01/36489 | 5/2001 |
| WO | WO 01/58957 | 8/2001 |
| WO | WO 02/0202143 | 1/2002 |
| WO | WO 02/066514 | 8/2002 |
| WO | WO 02/072605 | 9/2002 |
| WO | WO 02/079232 | 10/2002 |
| WO | WO 02/079415 | 10/2002 |
| WO | WO 02/090566 | 11/2002 |
| WO | WO 03/015697 | 2/2003 |
| WO | WO 03/048334 | 6/2003 |
| WO | WO 03/077834 | 9/2003 |

OTHER PUBLICATIONS

Mullins et al., Cancer Immunol. Immunother. 45:20-28, 1997.*
Mullins et al Immunopharmacology and Immunotoxicology 20:473-492, 1998.*
Chang et al Cancer Res. 54;1286-1291, 1994.*
Zagozdzon et al International Journal of Molecular Medicine 4:645-648, 1999.*
Chang et al Cancer Res. 54:1286-1291, 1994.*
Cividalli et al (J. Cancer Res. Clin. Oncol.; 1998, 124-236-244).*
Tentori et al (Cancer Immunol Immunother.; 1995, 41:375-383).*
U.S. Appl. No. 07/348,237, filed May 5, 1989, Rosenblum et al.
Abaza et al., (1992), "Effects of Amino Acid Substitutions Outside an Antigenic Site on Protein Binding to Monoclonal Antibodies of Predetermined Specificity Obtained by Peptide Immunization" *Journal of Protein Chemistry*, 11:5:433-444.
Abstract XP-002116766, (1996), "Prostaglandins, their inhibitors and cancer" *Prostaglandins, Leukotrienes and Essential Fatty Acids*, 54:2:83-94.
Afonso et al., (1994), "The Adjuvant Effect of Interleukin-12 in a Vaccine Against Leishmania Major," *Science*, 263:235-237.
Arenberg et al. (1996), "Interferon-γ-inducible Protein 10 (IP-10) Is an Angiostatic Factor That Inhibits Human Non-small Cell Lung Cancer (NSCLC) Tumorigenesis and Spontaneous Metastases," *J. Exp. Med*, 184:981-992.
Bacha et al., (1988),. "Interleukin 2 Receptor-Targeted Cytotoxicity Interleukin 2 Receptor-mediated Action of a Diphtheria Toxin-related Interleukin 2 Fusion Protein", *J. Experimental Medicine*, 167:612-622.
Bachelot et al., (Mar. 1998), "Retrovirus-Mediated Gene Transfer of an Angiostatin-Endostatin Fusion protein with Enhanced Anti-Tumor Properties In Vivo", *Proceedings of the Annual Meeting of the American Association for Cancer Research*, 39:271, Abstract # 1856.
Barnett et al. (1994), "Purification, characterization and selective inhibition of human prostaglandin G/H synthase 1 and 2 expressed in the baculovirus system," *Biochimica et Biophysica Acta*, 1209:130-139.
Abselga, et al (1998), "Recombinant Humanized Anti-HER2 Antibody (Herceptin™) Enhances the Antitumor activity of Paclitazel and Doxorubicin against HER3/*neu* Overexpressing Human Breast Cancer Xenografts." *Cancer Research*, 58:2825-2831.
Batova et al., (1999), "The Ch 14.18-GM-CSF Fusion Protein Is Effective at Mediating Antibody-dependent Cellular Cytotoxicity and Complement-dependent Cytotoxicity in Vitro," *Clinical Cancer Research*. 5:12:4259-4263.
Becker et al., (1996), "An Antibody-Interleukin 2 Fusion Protein Overcomes Tumor Heterogeneity by Induction of a Cellular Immune Response," *Proc. Natl. Acad. Sci.*, 93:7826-7831.
Becker et al., (1996), "Eradication of human hepatic and pulmonary melanoma metastases in SCID mice by antibody-interleukin 2 fusion proteins," *Proc. Natl. Acad. Sci. USA*, 93:2702-2707.
Beutler et al., (1988), "Tumor Necrosis, Cachexia, Shock, and Inflammation: A Common Mediator," *Ann. Rev. Biochem.*, 57:505-518.
Bissery et al., (1997), "Cancer Therapeutics: Experimental and Clinical Agents," *Ch. 8. Teicher, ed.* 175-193.
Bjorn et al., (1985), "Evaluation of Monoclonal Antibodies for the Development of Breast Cancer Immunotoxins," *Cancer Research*, 45:1214-1221.
Boehm et al., (1997), "Antiangiogenic therapy of experimental cancer does not induce acquired drug resistance," *Nature*, 390:404-407.
Boehm et al., (1998), "Zinc-Binding of Endostatin Is Essential for Its Antiangiogenic Activity," *Biochemical and Biophysical Research Communications*, 252:190-194.
Brooks et al., (1994), "Integrin $\alpha\beta_3$ Antagonists Promote Tumor Regression by Inducing Apoptosis of Angiogenic Blood Vessels," *Cell*, 79:1157-1164.
Buchli et al., (1993), "Structural and Biologic Properties of a Human Aspartic Acid-126 Interleukin-2 Analog," *Archives of Biochemistry and Biophysics*, 307:2:411-415.
Burgess et al., (1990), "Possible Dissociation of the heparin-binding and Mitogenic Activities of Hepari-binding (Acidic Fibroblast) Growth Factor-1 fromIts Receptor-binding Activities by Site-directed Mutagenesis of a Single Lysine Residue," *Journal of Cell Biology*, 111:2129-2138.
Canfield et al., (1991), "The Binding Affinity of Human IgG for its High Affinity Fc Receptor is Determined by Multiple Amino Acids in the CH2 Domain and Is Modulated by the Hinge Region," *Journal of Experimental Medicine*, 173:6:1483-1491.
Cao et al., (1996), "Kringle Domains of Human Angiostatin," *The Journal of Biological Chemistry*, 271:46:29461-29467.
Cao et al., (1997), "Kringle 5 of Plasminogen is a Novel Inhibitor of Endothelial Cell Growth," *The Journal of Biological Chemistry*, 272:36:22924-22928.
Capon et al., (1989), "Designing CD4 immunoadhesins for AIDS thearpy," *Nature*, 337:525-531.
Caton et al., (1986), "Structural and functional implications of a restricted antibody response to a defined antigenic region on the influenza virus hemagglutinin," *The EMBO Journal*, 5:7:1577-1587.
Chan et al., (1991), "Induction of Interferon ᵧProduction by Natural Killer Cell Stimulatory Factor: Characterization of the Responder Cells and Synergy with Other Inducers," *J. Exp. Med.*, pp. 869-879.
Chang et al., (1989), "Overview of Interleukin-2 as an Immunotherapeutic Agent," *Seminars in Surgical Oncology*, 5:385-390.
Chang et al., (1996), "A Point Mutation in Interleukin-2 that Alters Ligand Internalization," *Journal of Biological Chemistry*, 271:23:13349-13355.
Chaudhary et al., (1988), "Selective killing of HIV-infected cells by recombinant human CD4-Pseudomonas exotoxin hybrid protein," *Nature*, 335:370-372.
Chaudhary et al., (1989), "A recombinant immunotoxin consisting of two antibody variable domains fused to Pseudomonas exotoxin" *Nature*, 339:394-397.
Chen et al., (1997), "Eradication of Murine Bladder Carcinoma by Intratumor Injection of a Bicistronic Adenoviral Vector Carrying cDNAs for the IL-12 Heterodimer and Its Inhibition by the IL-12 p40 Subunit Homodimer," *Journal of Immunology*, 159:1:351-358.
Cheon et al., (1994), "High-affinity binding sites for related fibroblast growth factor ligands reside within different receptor immunoglobulin-like domains," *Proc. Natl. Acad. Sci. USA*, 91:989-993.

Chuang et al., (1993), "Effect of new investigational drug taxol on oncolytic activity and stimulation of human lymphocytes," *Gynecol. Oncol.*, 49:291-298.

Cohen, S. L. et al., (1996), "Human leptin characterization," *Nature*, 382:589.

Cole et al., (1997), "Human IgG2 Variants of Chimeric Anti-CD3 Are Nonmitgenic to T Cells," *Journal of Immunology*, 159:3613-3621.

Collins et al., (1988), "Identification of Specific Residues of Human Interleukin 2 that Affect Binding to the 70-kDa Subunit (p70) of the Interleukin 2 Receptor," *Proc. Natl. Acad. Sci*, 85:7709-7713.

Colombo et al., (1996), "Amount of Interleukin 12 Available at the Tumor Site is Critical for Tumor Regression," *Cancer Research*, 56:2531-2534.

D'Amato et al., (1994), "Thalidomide is an inhibitor of aniogenesis," *Proc. Natl. Acad. Sci. USA*, 91:4082-4085.

D'Andrea et al., (1992), "Production of Natural Killer Cell Stimulatory Factor (Interleukin 12) by Peripheral Blood Mononuclear Cells," *J. Exp. Med.*, 176:1387-1398.

Ding et al., (1988), "Zinc-Dependent Dimers Observed in Crystals of Human Edostatin," *Proceedings of the National Academy of Sciences of USA*, 95:10443-10448.

Earnest et al., (1992), "Piroxicam and Other Cyclooxygenase Inhibitors: Potential for Cancer Chemoprevention," *J. Cell. Biochem. Supp*, 161:156-166.

Eisenthal, (1990), "Indomethacin up-regulated the generation of lymphokine-activated killer-cell activity and antibody-dependent cellular cytotoxicity mediated by interleukin-2," *Cancer Immunol. Immunotherap.* 31:342-348.

Fell et al., (1991), "Genetic Construction and Characterization of Fusion Protein consisting of a Chimeric F(ab') with Specificity for Carcinomas and Human IL-2," *The J. of Immunology*, 146:7:2446-2452.

Fell et al., (1992), "Chimeric L6 antitumor antibody," *The J. of Biol. Chem.*, 267:15552-15558.

Friedman, J. M. et al., (1998), "Leptin and the regulation of body weight in mammals," *Nature*, 395:763-770.

Gasson et al., (1984), "Purified Human Granulocyte Macrophage Colony-Stimulating Factor: Direct Action on Neutrophils," *Science*, 226:1339-1342.

Gately et al., (1998), "The Interleukin-12/Interleukin-12 Receptor system: Role in Normal and Pathologic Immune Responses," *Annu. Rev. Immunol.*, 16:495-521.

Gillessen et al., (1995), "Mouse Interleukin-12 (IL-12) p40 Homodimer: A Potent IL-12 Antagonist" *Eur. J. Immunol.*, 25:200-206.

Gillies et al., (1989), "Expression of Human Anti-Tetanus toxoid antibody in Transfected Murine Myeloma Cells," *Bio/Technology*, 7:799-804.

Gillies et al., (1989), "High-Level Expression of Chimeric Antibodies Using Adapted cDNA Variable Region Cassettes," *J. Immunol. Methods*, 125:191-202.

Gillies et al., (1990), "Antigen binding and biological activities of engineered mutant chimeric antibodies with human tumor specificities," *Hum. Antibod. Hybridomas*, 1:1:47-54.

Gillies et al., (1992), "Antibody-Targeted Interleukin 2 Stimulates T-Cell Killing of Autologous Tumor Cells," *Proc. Natl. Acad. Science*, 89:1428-1432.

Gillies et al., (1993), "Biological Activity and In Vivo Clearance of Antitumor Antibody/Cytokine Fusion Proteins," *Bioconjugate Chem.*, 4:230-235.

Gillies, et al., (1998), "Antibody-IL-12 fusion proteins are effective in SCID mouse models of prostrate and colon carcinoma matastases," *Journal Immunology*, 160:2:6195-6203.

Gillies, et al., (1999), "Improving the efficacy of antibody-interleukin 2 fusion protiens by reducing their interaction with Fc receptors," *Cancer Research*, 59:2159-2166.

Gillis et al., (1978), "T Cell Growth Factor: Parameters of Production And A Quantitative Microassay for Activity," *Journal of Immunology*, 120:6:2027-2032.

Goeddel et al., (1986), "Tumor Necrosis Factors; Gene Structure and Biological Activities," *Pharm. Sciences*, pp. 597-609.

Gren et al., (1983), "A New Type of Leukocytic Interferon," *Dokl. Biochem.*, 269:91-95.

Griffon-Etienne et al., (1999), "Taxane-induced apoptosis decompresses blood vessels and lowers interstitial fluid pressure in solid tumors: clinical implications," *Cancer Research*, 59:3776-3782.

Grimaldi et al., (1989), "The t(5;14) Chromosomal Translocation in a Case of Acute Lymphocytic Leukemia Joins the Interleukin-3 Gene to the Immunoglobulin Heavy Chain Gene," *Blood*, 73:8:2081-2805.

Guyre et al., (1997), "Increased potency of Fc-receptor-targeted antigens," *Cancer Immunol. Immunother* 45:146-148.

Harris et al., (1993), "Therapeutic Antibodies—the Coming of Age" *Tibtech*, 11:42-44.

Harvill et al., (1996), "In vivo properties of an IgG3-IL-2 fusion protein: A general strategy for immune potentiation," *Journal of Immunology*, 157:7:3165-3170.

Hazama et al., (1993), "Adjuvant-Independent Enhanced Immune Responses to Recombinant Herpes Simplex Virus Type 1 Glycoprotein D by Fusion with Biologically Active Interleukin-2," *Vaccine*, 11:6:629-636.

He et al., (1998), "Humanization and Pharmacokinetics of Monoclonal Antibody with Specificity for Both E- and P-Selectin," J. Immunol., 1029-1035.

Heijnen et al., (1996), "Antigen Targeting to Myeloid-specific Human FcYRI/CD64 Triggers Enhanced Anitbody Responses in Transgenic Mice," *J. Clin. Invest.*, 97:2:331-338.

Heinzel et al., (1997), "In Vivo Production and Function of IL-12 p40 Homodimers" In Vivo Biology of IL-12 p40 Homodimer, *Journal of Immunology*, 158-4381-4388.

Hellstrom et al., (1986), "Antitumor effects of L6, and IgG2a antibody that reacts with most human carcinomas," *Proc. Natl. Acad. Sci.*, 83:18: 7059-7063.

Henkart, (1985), "Mechanism of Lymphocyte-Mediated Cytotoxicity," *Ann. Rev. Immunol.*, 3:31-58.

Herrmann et al., (1989), "Hematopoeitic Responses With Advanced Malignancy Treated With Recombinant Human Granulocyte-Macrophage Colony-Stimulating Factor," *Journal of Clinical Oncology*, 7:2:159-167.

Hohenester et al., (1998), "Crystal Structure of the Angiogenesis Inhibitor Endostatin at 1/5 Å Resolution," *EMBO Journal*, 17:6:1656-1664.

Holden et al., (2001), "Augmentation of Anti-Tumor Activity of KS-Il2 Immunocytokine with Chemotherapeutic Agents." *Proceedings of the American Association for Cancer Research*, 42:683, Abstract No. 3675.

Holden et al., (2001). "Augmentation of Antitumor activity of an Antibody-Interleukin 2 Immunocytokine with Chemotherapeutic Agents" *Clinical Cancer Research*, 7:2862-2869.

Hoogenboom et al., (1991), "Construction and expression of antibody-tumor necrosis factor fusion proteins," *Molecular Immunology*, 28:9:1027-1037.

Hoogenboom et al., (1991), "Targeting of Tumor Necrosis Factor to Tumor Cells Secretion by Myeloma Cells of a Genetically Engineered Antibody-Tumor Necrosis Factor Hybrid Molecule," *Biochim. and Biophys. Acta*, 1096:4:345-354 (Abstract).

Hornick et al, (1999), "Pretreatment with a monoclonal antibody/ interleukin-2 fusion protein directed against DNA enhances the delivery of therapeutic molecules to solid tumors," *Clin. Cancer Res.*, 5:51-60.

Hu et al., (1996), "A Chimeric Lym-1/Interleukin 2 Fusion Protein for Increasing Tumor Vascular Permeability and Enhancing Antibody Uptake'," *Cancer Research*, 56:4998-5004.

Huck et al., (1986), "Sequence of a human immunoglobulin gamma 3 heavy chain constant region gene: comparison with the other human Cγ genes," *Nucleic Acids Research*, vol. 14:4:1779-1789.

Huse et al., (1989), "Generation of a Large Combinatorial Library of the Immunoglobulin Repertoire in Phage Lambda," *Science*, 246:1275-1281.

Ingber et al., (1990), "Synthetic analogues of fumagillin that inhibit angiogensis and suppress tumour growth," *Nature*, 348:555-557.

Jones et al., (1986), "Replacing the complementarity-determining regions in a human antibody with those from a mouse," *Nature*, 321:6069:522-525.

Ju et al., (1987), "Structure-Function Analysis of Human Interleukin-2," *Journal of Biological Chemistry*, 262:12:5723-5731.

Jung et al., (1986), "Activation of human peripheral blood mononuclear cells by anti-T3: Killing of tumor target cells coated with anti-target-anti-T3 conjugates," *Proc. Natl. Acad. Sci.*, 83:4479-4483.

Junghans et al., (1996), "The protection receptor of IgG catabolism is the B2-micorgobulin-containing neonatal intestinal transport receptor," *Proc. Natl. Acad. Sci.*, 93:11:5512-5516.

Kang et al., (1991), "Antibody redesign by chain shuffling from random combinatorial immunoglobulin libraries," *Proc. Natl. Acad. Sci.*, 88:11120-11123.

Kappel, et al., (1992), "Regulating gene expression in transgenic animals," *Current Opinion in Biotechnology* 3:548-553.

Karpovsky et al., (1984), "Production of Target-Specific Effector Cells using Hetero-Cross Linked Aggregate Containing Anti-Target Cell and AntiFcλ Receptor Antibodies," *Journal of Experimental Medicine*, 160:6:1686-1701.

Kendra et al., (1999), "Pharmacokinetics and stability of the ch 14.18-interleukin-2 fusion protein in mice," *Cancer Immunol. Immunotherapy*, 48;219-229.

Kim, et al., (1997), "An Ovalbumin-IL-12 fusion protein is more effective than oval bumin plus free recombinant IL-12 in inducing a T helper cell type 1-dominated immune response and inhibiting antigen-specific IgE production." *Journal Immunology*, 158:9:4137-4144.

Kim, et al., (1999), "Cytokine Molecular Adjuvants Modulate Immune Responses Induced by DNA Vaccine Constructs for HIV-1 and SIV" *Journal of Interferon and Cytokine Research*, 19:77-84.

Kranz et al., (1984), "Attachment of an anti-receptor antibody to non-target cells renders them susceptible to lysis by a clone of cytotoxic T lymphocytes", *Proc. Natl. Acad. Sci.*, 81:7922-7926.

Kuo, et al., (2001), "Oligomerization-dependent Regulation of Motility and Morphogenesis by the Collagen XVIII NC1/Endostatin Domain," *Journal of Cell Biology*, 152:6:1233-1246.

LaVallie et al., (1993), "Cloning and Functional Expression of a cDNA Encoding the Catalytic Subunit of Bovine Enterokinase," *Journal of Biological Chemistry*, 268:31:23311-23317.

Lazar et al., (1998), "Transforming Growth Factor α: Mutation of Aspartic Acid 47 and Leucine 48 Results in Different Biological Activities," *Molecular and Cellular Biology*, 8:3:1247-1252.

LeBerthon et al., (1991), "Enhanced Tumor Uptake of Macromolecules Induced by a Novel Vasoactive Interleukin 2 Immunoconjugate," *Cancer Research*, 51:2694-2698.

Lieschke, et al., (1997), "Bioactive murine and human interleukin-12 fusion proteins which retain antitumor activity in vivo," *Nature Biotechnology*, 15:1:35-40.

Linsley et al., (1991), "CTLA-4 is a Second Receptor for B Cell Activation Antigen B7," *Journal of Experimental Medicine*, 174:3:561-569.

Liu et al., (1985), "Heteroantibody Duplexes Target Cells for Lysis by Cytotoxic T Lymphocytes", *Proc. Natl. Acad. Sci.*, 82:8648-8652.

Liu et al., (1988), "Hormone Conjugated with Antibody to CD3 Mediates Cytotoxic T Cell Lysis of Human Melanoma Cells," *Science*, 239:395-398.

Liu et al., (1998), "Immunostimulatory CpG Oligodeoxynucleotides Enhance the Immune Response to Vaccine Strategies Involving Granulocyte-Macrophage Colony-Stimulating Factor," *Blood*, 92:10:3730-3736.

Lo et al., (1998), "High Level Expression and Secretion of Fc-X Fusion Proteins in Mammalian Cells" *Protein Engineering*, 11:6:495-500.

Lode et al., (1998), "Immunocytokines: a promising approach to cancer immunotherapy," *Pharmacol. Thera.*, 80:3:277-292.

Lode et al., (1998), "Natural Killer Cell-Mediated Eradication of Neuroblastoma Metastases to Bone Marrow by Targeted Interleukin-2 Therapy," *Blood*, 91:5:1706-1715.

Lode et al., (1999), "Synergy between an antiangiogenic integrin $\alpha_v$ antagonist and an antibody-cytokine fusion protein eradicates spontaneous tumor metastases," *Proc. Natl. Acad. Sci.*, 96:1591-1596.

Lode et al., (1999), "Tumor-targeted IL-2 amplifies T cell-mediated immune response induced by gene therapy with single-chain IL-12," *Proc. Natl. Acad. Sci.*, 96:8591-8596.

Lode et al., (2000), "Amplification of T Cell Mediated Immune Responses by Antibody-Cytokine Fusion Proteins," *Immunological Investigations*, 29:2:117-120.

Maloney et al., (1994), "Phase I Clincal Trial Using Escalating Single-Dose Infusion of Chimeric Anti-CD20 Monoclonal Antibody (IDEC-C2B8) in Patients with Recurrent B-Cell Lymphoma," *Blood*, 84:8:2457-2466.

Mark et al., (1992), "Expression and characterization of hepatocyte growth factor receptor IgG fusion proteins." *Journal of Biological Chemistry*, 267:36:26166-26171.

Martinotti et al., (1995), "CD4 T Cells Inhibit in vivo the CD8-Mediated Immune Response Against Murine Colon Carcinoma Cells Transduced with Interleukin-12 Genes," *Eur. J. Immunol.* 25:137-146.

Medesan et al., (1997), "Delineation of the Amino Acid Residues Involved in Transcytosis and Catabolism of Mouse IgG1, " *Journal Immunology*, 158:5:2211-2217.

Mestre et al., (1997), "Retinoids Suppress Epidermal Growth Factor-induced Transcription of cyclooxygenase-2 in Human Oral Squamous Carcinoma Cells," *Cancer Research*, 57:2890-2895.

Mosmann et al., (1989), "TH1 and TH2 Cells: Different Patterns of Lymphokine Secretion Lead to Different Functional Properties," *Ann. Rev. Immunol*, 7:145-173.

Mott et al., (1995), "The Solution Structure of the F42A Mutant of Human Interleukin 2," *J. Mol. Biol.*, 247:979-994.

Mullins et al., (1998), "Interleukin-12 overcomes paclitaxel-mediated suppression of T-cell proliferation," *Immunopharmacol. Immunotoxicol.*, 20:4:473-492.

Murphy et al., (1986), "Genetic construction, expression, and melanoma-selective cytotoxicity of a diptheria toxin-related α-melanocyte-stimulating hormone fusion protein," *Proc. Natl. Acad. Sci.*, 83:8258-8262.

Murphy, (1988), "Diphtheria-related peptide hormone gene fusions: A molecular gene approach t chimeric toxin development," *Immunotoxins*, 123-140.

Nedwin et al., (1985), "Human Lymphotoxin and Tumor Necrosis Factor Genes: Structure, Homology and Chromosomal Localization," *Nucleic Acids Research*, 13:17:6361-6373.

Netti et al., (1995), "Time-dependent behavior of interstitial fluid pressure in solid tumors: implications for drug delivery," *Cancer Research*, 55:5451-5458.

Netti et al., (1999), "Enhancement of fluid filtration across tumor vessels: implication for delivery of macromolecules," *Proc. Nat. Acad. Sci*, 96:3137-3142.

Neuberger, et al., (1984), "Recombinant Antibodies Possessing Novel Effector Functions.," *Nature*, 312:604-608.

O'Reilly et al., (1994), "Angiostatin: A Novel Angiogenesis Inhibitor That Mediates the Suppression of Metastases by a Lewis Lung Carcinoma," *Cell*, 79:315-328.

O'Reilly et al., (1996), "Angiostatin induces and sustains dormancy of human primary tumors in mice," *Nature Medicine*, 2:6:689-692.

O'Reilly et al., (1997), "Endostatin: An Endogenous Inhibitor of Angiogenesis and Tumor Growth," *Cell*, 88:277-285.

Pastan et al., (1989), "Pseudomonas Exotoxin: Chimeric Toxins," *Journal of Biological Chemistry*, 264:26:15157-15160.

Paul et al., (1988), "Lymphotoxin," *Ann. Rev. Immunol.*, 6:407-438.

Perez et al., (1986), "Specific Targeting of Human Peripheral Blood T Cells by Heteroaggregates Containing Anti-T3 Crosslinked to Anti-Target cell antibodies," *J. Exp. Medicine*, 163:166-178.

Perez et al., (1989), "Isolation and Characterization of a cDNA Encoding the KSI/4 Epithelial Carcinoma Marker," *Journal Immunology*, 142:10:3662-3667.

Polizzi et al., (1999), "A novel taxane with improved tolerability and therapeutic activity in a panel of human tumor xenografts," *Cancer Research*, 59:1036-1040.

Putzer et al., (1997), "Interleukin 12 and B7-1 Costimulatory Molecule Expressed by an Adenovirus Vector Act Synergistically to Facilitate Tumor Regression," *Proc. Nat'l Acad. Sci.*, 94:20:10889-10894.

Reisfeld et al., (1996), "Recombinant antibody fusion proteins for cancer immunotherapy," *Current Topics in Microbiology and Immunology*, 27-53.

Reisfeld et al., (1997), "Immunocytokines: a new approach to immunotherapy of melanoma," *Melanoma Research*, 7:2:S99-S106.
Riethmuller et al., (1994), "Randomised trial of monoclonal antibody for adjuvant therapy of resected Dukes' C colorectal carcinoma," *The Lancet*, 343:1177-1183.
Roessler et al., (1994), "Cooperative Interactions between the interleukin 2 receptor α and β chains alter the interleukin 2-bindign affinity of the receptor subunits," *Proc. Natl. Acad. Sci.*, 91:3344-3347.
Roitt et al., (1993), "The Role of TH Cells in the Selection of Effector Mechanisms Directed Against Target Antigens," *Immunology*, Third Edition, 8.3-8.4.
Rosenberg, (1988), "Immunotherapy of Cancer Using Interleukin 2: current status and future prospects," *Immunology Today*, 9:2:58-62.
Rozwarski et al., (1994), "Structural comparisons among the short-chain helical cytokines," *Structure 2*, 2:3:159-173.
Santon et al., (1986), "Effects of Epidermal Growth Factor Receptor Concentration on Tumorigenicity of A431 Cells in Nude Mice," *Cancer Research*, 46:4701-4705.
Sasaki et al., (1998), "Structure, function and tissue forms of the C-terminal globular domain of collagen XVII containing the angiogenesis inhibitor endostatin," *The EMBO Journal*, 17:15:4249-4256.
Sauve et al., (1991), "Localization in human interleukin 2 of the binding site of the α chain (p55) of the interleukin 2 receptor," *Proc. Natl. Acad. Sci.*, 88:4636-4640.
Schnee et al., (1987), "Construction and expression of a recombinant antibody-targeted plasminiogen activator," *Proc. Natl. Acad. Sci.*, 84:6904-6908.
Schoenhaut et al., (1992), "Cloning and Expression of Murine IL-12," *Journal of Immunology*, 148:11:3433-3340.
Senter et al., (1988), "Anti-tumor effects of antibody-alkaline phosphatase conjugates in combination with etoposide phosphate," *Proc. Natl. Acad. Sci.*, 85:13:4842-4846.
Shanafelt et al., (2000), "A T-cell-selective interleukin 2 mutein exhibits potent antitumor activity and is well tolerated in vivo," *Nature Biotechnology*, 18:1197-1202.
Sharma et al., (1999), "T cell-derived IL-10 promotes lung cancer growth by suppressing both T cell and APC function," *Journal Immunology.*, 163:5020-5028.
Shen et al., (1986), "Heteroantibody-Mediated Cytotoxicity: Antibody to the High Affinity Fc Receptor for IgG mediates cytotoxicity by Human Monocytes that is enhanced by interferon-λ and is not blocked by human IgG," *Journal of Immunology*, 137:11:3378-3382.
Shiff et al., (1995), "Sulindac Sulfide, an Asprin-like Compound, Inhibits Proliferation, Causes Cell Cycle Quiescence, and Induces Apoptosis in HT-29 Colon Adenocarcinoma Cells," *Journal of Clinical Investigation*, 96:491-503.
Shin et al., (1990), "Expression and characterization of an antibody binding specificity joined to insulin-like growth factor 1: Potential applications for cellular targeting," *Proc. Natl. Acad. Sci.*, 87:5322-5326.
Sim et al., (1997), "A Recombinant Human Angiostatin Protein Inhibits Experimental Primary and Metastatic Cancer," *Cancer Research*, 57:1329-1334.
Stevenson et al., (1997), "Conjugation of Human Fcγ in Closed-Hinge or Open-Hinge Configuration to Fab'γ and Analogous Ligands," *Journal of Immunology*, 158:2242-2250.
Sulitzeanu et al., (1993), "Immunosuppressive factors in human cancer," *Adv. Cancer Research*, 60:247-267.
Taniguchi et al., (1983), "Structure and expression of a cloned cDNA for human interleukin-2," *Nature*, 302:305-309.
Tao et al., (1989), "Studies of Aglycosylated Chimeric Mouse IgG: Role of Carbohydrate in the Structure and Effector Functions Mediated by the Human IgG Constant Region," *Journal of Immunology*, 143:8:2595-2601.
Tao et al., (1993), "Structural Features of Human Immunoglobulin G that Determine Isotype-Differences in Copmlement Activation," *Journal of Experimental Medicine*, 178:2:661-667.
Teicher et al., (1994), "Potentiation of Cytotoxic Cancer Therapies by TNP-470 Alone and With Other Anti-Angiogenic Agents," *Int. J. Cancer*, 57:920-925.

*The Merck Manual of Diagnosis and Therapy*, 990-993, 1278-1283 (17th ed. 1999).
Till et al., (1988), "An Assay that Predicts the Ability of Monoclonal Antibodies to Form Potent Ricin A Chain-containing Immunotoxins," *Cancer Research*, 48:5:1119-1123.
Till et al., (1988), "HIV-Infected Cells are Killed by rCD4-Ricin A Chain," *Science*, 242:1166-1168.
Trinchieri, (1994), "Interleukin-12: A Cytokine Produced by Antigen-Presenting Cells With Immunoregulatory Functions in the Generation T-Helper Cells Type 1 and Cytotoxic Lymphocytes," *Blood*, 84:4008-4027.
Vagliani et al., (1996), "Interleukin 12 Potentiates the Curative Effect of a Vaccine Based on Interleukin 2-transduced Tumor Cells," *Cancer Research*, 56:467-470.
Varki et al., (1984), "Antigens Associated with a human lung adenocarcinoma defined by monoclonal antibodes," *Cancer Research*, 44:681-687.
Verhoeyen et al., (1988), "Reshaping Human Antibodies: Grafting an Antilysozyme Activity," *Science*, 239:1534-1536.
Villunger et al., (1997), "Constitutive expression of Fas (Apo-1/CD95) ligand on multiple myeloma cells: a potential mechanism of tumor-induced suppression of immune surveillance," *Blood*, 90:1:12-20.
Watanabe et al., (1997), "Long-term depletion of naive T cells in patients treated for Hodgkin's disease," *Blood*, 90:9:3662-3672.
Williams et al., (1986), "Production of antibody-tagged enzymes by myeloma cells: application to DNA polymerase I Klenow fragment," *Gene*, 43:319-324.
Williams et al., (1987), "Diphtheria toxin receptor binding domain substitution with interleukin-2: genetic construction and properties of a diphtheria toxin-related interleukin-2 fusion protein," *Protein Engineering*, 1:6:493-498.
Wooley et al., (1993), "Influence of a Recombitant Human Soluble Tumor Necrosis Factor Receptor FC Fusion Protein on Type II Collagen-Induced Arthritis in Mice," *Journal Immunology*, 151:6602-6607.
Wu et al.,(1997), "Suppression of Tumor Growth with Recombinant Murine Angiostatin," *Biochemical and Biophysical Research Communications*, 236:651-654.
Xiang et al., (1997), "Elimination of Established Murine Colon Carcinoma Metastases by Antibody-Interleukin 2 Fusion Protein Therapy," *Cancer Research*, 57:4948-4955.
Xin Xau Zheng, et al., (1995), "Administration of nonstyolytic IL-10/Fc in muring models of lipopolysaccaride-induced septic shock and allogenic islet transplantation," *Journal Immunology*, 154:5590-5600.
Angal et al., (1993), "A Single Amino Acid Substitution Abolishes the Heterogeneity of Chimeric Mouse/Human (IgG4) Antibody," *Molecular Immunology*, 30(1):105-108.
Batra et al., (1993), "Insertion of Constant Region Domains of Human IgG1 into CD4-PE40 Increases Its Plasma Half-Life," *Molecular Immunology*, 30(4):379-386.
Becker et al., (1996), "Long-lived and Transferable Tumor Immunity in Mice after Targeted Interleukin-2 Therapy," *J. Clin. Invest.*, 98(12):2801-2804.
Becker et al., (1996), "T Cell-mediated Eradication of Murine Metastatic Melanoma Induced by Targeted Interleukin-2 Therapy," *J. Exp. Med.*, 183(50):2361-2366.
Bitonti et al., (2002), "Transepithelial Absorption of an Erythropoietin-Fc Fusion Protein After Delivery to the Central Airways," *Respiratory Drug Delivery*, 8:309-312.
Boissel et al., (1993), "Erythopoietin Structure-Function Relationships: Mutant Proteins that Test a Model of Tertiary Structure," *The Journal of Biological Chemistry*, 268(21):15983-15993.
Briggs et al., (1974), "Hepatic Clearance of Intact and Desialylated Erythropoietin," *American Journal of Physiology*, 227(6):1385-1388.
Cruse et al. (eds.), (1995), *Illustrated Dictionary of Immunology*, pp. 156-157, CRC Press, NY.
Darling et al., (2002), "Glycosylation of Erythropoietin Affects Receptor Binding Kinetics: Role of Electrostatic Interactions," *Biochemistry*, 41:14524-14531.

Davis et al., (2003), "Immunocytokines: Amplification of Anti-cancer Immunity," *Cancer Immunol. Immunother.*, 52:297-308.

Dolman et al., (1998), "Suppression of Human Prostate Carcinoma Metastases in Severe Combined Immunodeficient Mice by Interleukin 2 Immunocytokine Therapy," *Clin. Cancer Research.*, 4(10):2551-2557.

Duncan et al., (1988), "The Binding Site for C1q on IgG," *Nature*, 332:738-740.

Egrie et al., (2001), "Development and Characterization of Novel Erythropoiesis Stimulating Protein (NESP)," *Nephrol. Dial. Transplant.*, 16(Supp 3):3-13.

Elliott et al., (1997), "Mapping of the Active Site of Recombinant Human Erythropoietin," *Blood*, 89(2):493-502.

Fibi et al., (1995), "N- and O-Glycosylation Muteins of Recombinant Human Erythropoietin Secreted From BHK-21 Cells," *Blood*, 85(5):1229-1236.

Frost et al., (1997), "A Phase I/IB Trial of Murine Monoclonal Anti-GD2 Antibody 14.G2a Plus Interleukin-2 in Children with Refractory Neuroblastoma," *Cancer*, 80(2):317-333.

Gan et al., (1999), "Specific Enzyme-linked Immunosorbent Assays for Quantitation of Antibody-cytokine Fusion Proteins," *Clinical and Diagnostic Laboratory Immunology*, 6(2):236-42.

Gillies et al., (1991), "Expression of Genetically Engineered Immunoconjugates of Lymphotoxin and a Chimeric Anti-ganglioside GD2 Antibody," *Hybridoma.*, 10(3):347-56.

Gillies et al., (2002), "Bi-functional Cytokine Fusion Proteins for Gene Therapy and Antibody-targeted Treatment of Cancer," *Cancer Immunol. Immunother.*, 51(8):449-60.

Gillies et al., (2002), "Improved Circulating Half-life and Efficacy of an Antibody-interleukin 2 Immunocytokine Based on Reduced Intracellular Proteolysis," *Clin. Cancer Research*, 8(1):210-216.

Greene et al., (1975), "Neuronal Properties of Hybrid Neuroblastoma X Sympathetic Ganglion Cells," *Proc. Natl. Acad. Sci. USA*, 72(12): 4923-4927.

Hammerling et al., (1996), "In Vitro Bioassay for Human Erythropoietin Based on Proliferative Stimulation of an Erythroid Cell Line and Analysis of Carbohydrate-dependent Microheterogeneity," *Journal of Pharmaceutical and Biomedical Analysis*, 14:1455-1469.

Hank et al., (1996), "Activation of Human Effector Cells by a Tumor Reactive Recombinant Anti-ganglioside GD2 Interleukin-2 Fusion Protein (ch14.18-IL2)," *Clin Cancer Research*, 2(12):1951-1959.

Hank et al., (2003), "Determination of Peak Serum Levels and Immune Response to the Humanized Anti-ganglioside Antibody-interleukin-2 Immunocytokine," in *Methods in Molecular Medicine, vol. 85: Novel Anticancer Drug Protocols*, Buolamwini et al., (eds.), pp. 123-131, Humana Press Inc., Totowana, NJ.

Haraguchi, (1994), "Isolation of GD3 Synthase Gene by Expression Cloning of GM3 α-2,8-sialyltransferase cDNA using anti-GD2 Monoclonal Antibody," *Proc. Natl. Acad. Sci. USA*, 91(22):10455-10459.

Harris, (1995), "Processing of C-terminal Lysine and Arginine Residues of Proteins Isolated from Mammalian Cell Culture," *J. Chromatography A*, 705:129-134.

Harvill et al., (1995), "An IgG3-IL2 Fusion Protein Activates Complement, Binds FcγRI, Generates LAK Activity and Shows Enhanced Binding to the High Affinity IL-2R," *Immunotechnology*, 1:95-105.

Hezareh et al., (2001), "Effector Function Activitities of a Panel of Mutants of a Broadly Neutralizing Antibody against Human Immunodeficiency Virus Type 1," *J. Virology*, 75(24):12161-12168.

Idusogie et al., (2000), "Mapping of the C1q Binding Site on Rituxan, a Chimeric Antibody with a Human IgG1 Fc," *J. Immunology*, 164(8):4178-4184.

Imboden et al., (2001), "The Level of MHC Class I Expression on Murine Adenocarcinoma Can Change the Antitumor Effector Mechanism of Immunocytokine Therapy," *Cancer Research*, 61(4):1500-7.

Kato et al., (1997), "Mechanism for the Nonlinear Pharmacokinetics of Erythropoietin in Rats," *The Journal of Pharmacology and Experimental Therapeutics*, 283:520-527.

Kato et al., (1998), "Pharmacokinetics of Erythopoietin in Genetically Anemic Mice," *Drug Metabolism and Disposition*, 26(2):126-131.

Kitamura et al., (1989), "Establishment and Characterization of a Unique Human Cell Line that Proliferates Dependently on GM-CSF, IL-3 or Erythropoietin," *Journal of Cellular Physiology*, 140:323-334.

Kushner et al., (2001), "Phase II Trial of the Anti-GD2 Monoclonal Antibody 3F8 and Granulocyte-Macrophage Colony-Stimulating Factor for Neuroblastoma," *J. Clinical Oncology*, 19(22):4189-94.

Locatelli et al., (2001), "Darbepoetin alfa Amgen," *Current Opinion in Investigational Drugs*, 2:1097-1104.

Lode et al., (1997), "Targeted Interleukin-2 Therapy for Spontaneous Neuroblastoma Metastases to Bone Marrow," *J. Natl. Cancer Inst.*, 89(21):1586-94.

Lode et al., (2000), "What To Do With Target IL-2," *Drugs of Today*, 36(5):321-336.

Lode et al., (2000), "Melanoma Immunotherapy by Targeted IL-2 Depends on CD4(+) T-cell Help Mediated by CD40/CD40L Interaction," *J. Clin. Invest.*, 105(11):1623-30.

Macdougall, (2002), "Optimizing the Use of Erythropoietic Agents—Pharmacokinetic and Pharmacodynamic Considerations," *Nephrol. Dial. Transplant.*, 17(Supp 5):66-70.

Metelitsa et al., (2002), "Antidisialoganglioside/granulocyte Macrophage-colony-stimulating Factor Fusion Protein Facilitates Neutrophil Antibody-dependent Cellular Cytotoxicity and Depends on FcγRII (CD32) and Mac-1 (CD11b/CD18) for Enhanced Effector Cell Adhesion and Azurophil Granule Exocytosis," *Blood*, 99(11):4166-73.

Mueller et al., (1997), "Humanized Porcine VCAM-specific Monoclonal Antibodies with Chimeric IgG2/G4 Constant Regions Block Human Leukocyte Binding to Porcine Endothelial Cells," *Molecular Immunology*, 34(6):441-452.

Naramura et al., (1994), "Mechanisms of Cellular Cytotoxicity Mediated by a Recombinant Antibody-IL2 Fusion Protein Against Human Melanoma Cells," *Immunology Letters*, 39:91-99.

Neal et al., (2003), "NXS2 Murine Neuroblastomas Express Increased Levels of MHC Class 1 Antigens upon Recurrence Following NK-dependent Immunotheapy," *Cancer Immunol. Immunother.*, 53:41-52.

Ngo et al., (1994), "Computation Complexity, Protein Structure Prediction, and the Levinthal Paradox," in *The Protein Folding Problem and Tertiary Structure Prediction*, Merz et al. (eds.), pp. 433-440 and 492-495, Birkhauser, Boston, MA.

Niethammer et al., (2002) "An Oral DNA Vaccine Against Human Carcinoembryonic Antigen (CEA) Prevents Growth and Dissemination of Lewis Lung Carcinoma in CEA Transgenic Mice," *Vaccine*, 20:421-429.

Niethammer et al., (2001) "Targeted Interleukin 2 Therapy Enhances Protective Immunity Induced by an Autologous Oral DNA Vaccine against Murine Melanoma," *Cancer Research*, 61(16):6178-84.

Nimtz et al., (1993), "Structures of Sialylated Oligosaccharides of Human Erythropoietin Expressed in Recombinant BHK-21 Cells," *Eur. J. Biochem.*, 213:39-56.

Pancook et al., (1996), "Eradication of Established Heatic Human Neuroblastoma Metastases in Mice with Severe Combined Immunodeficiency by Antibody-targeted Interleukin-2," *Cancer Immunol. Immunother.*, 42(2):88-92.

Park et al., (2000), "Efficiency of Promoter and Cell Line in High-level Expression of Erythropoietin," *Biotechnol. Appl. Biochem.*, 32:167-172.

Reisfeld et al., (1996), "Antibody-interleukin 2 fusion proteins: a new approach to cancer theraphy" *J Clin Lab Anal.*, 10(3):160-6.

Reisfeld et al., (1996), "Involvement of B Lymphocytes in the Growth Inhibition of Human Pulmonary Melanoma Metastases in Athymic *nu/nu* Mice by an Antibody-lymphotoxin Fusion Protein," *Cancer Research*, 56(8):1707-1712.

Ruehlmann et al., (2001), "MIG (CIXCL9) Chemokine Gene Therapy Combines with Antibody-cytokine Fusion Protein to Suppress Growth and Dissemination of Murine Colon Carcinoma," *Cancer Research*, 61(23):8498-503.

Sabzevari et al., (1994), "A Recombinant Antibody-interleukin 2 Fusion Protein Suppresses Growth of Hepatic Human Severe Combined Immunodeficiency Mice" *Proc. Natl. Acad. Sci. USA*, 91(20):9626-30.

Seidenfeld et al., (2001), "Epoietin Treatment of Anemia Associated with Cancer Therapy: A Systematic Review and Meta-analyis of Controlled Clinical Trials," *Journal of National Cancer Institute*, 93(16):1204-1214.

Shinkawa et al., (2003), "The Absence of Fucose But Not the Presence of Galactose or Bisecting N-Acetylglucosamine of Human IgG1 Complex-type Oligosaccharides Shows the Critical Role of Enhancing Antibody-dependent Cellular Cytotoxicity" *J. Biol. Chem.*, 278:3446-3473.

Spiekermann et al., (2002), "Receptor-mediated Immunoglobulin G Transport Across Mucosal Barriers in Adult Life: Functional Expression of FcRn in the Mammalian Lung," *J. Exp. Med.*, 196:303-310.

Syed et al., (1998), "Efficiency of Signaling Through Cytokine Receptors Depends Critically on Receptor Orientation," *Nature*, 395:511-516.

Thommesen et al., (2000), "Lysine 322 in the Human IgG3 CH2 Domain is Crucial for Antibody Dependent Complement Activation," *Mol. Immunol.*, 37(16):995-1004.

Wells, (1990), "Additivity of Mutation Effect in Proteins," *Biochemistry*, 29(37):8509-8517.

Wen et al., (1993), "Erythropoietin Structure-Function Relationships: High Degree of Sequence Homology Among Mammals," *Blood*, 82(5):1507-1516.

Xiang et al., (1998), "Induction of Persistent Tumor-protective Immunity in Mice Cured of Established Colon Carcinoma Metastases," *Cancer Research*, 58(17):3918-3925.

Xiang et al., (1999) "T Cell Memory against Colon Carcinoma is Long-lived in the Absence of Antigen," *J. Immunology*, 163(7):3676-83.

Xiang et al., (2001), "A Dual Function DNA Vaccine Encoding Carcinoembryonic Antigen and CD40 Ligand Trimer Induces T Cell-mediated Protective Immunity Against Colon Cancer in Carcinoembryonic Antigen-Transgenic Mice," *J. Immunology*, 167(8):4560-5.

Xiang et al., (2001), "Protective Immunity Against Human Carcinoembryonic Antigen (CEA) Induced by an Oral DNA Vaccine in CEA-transgenic Mice," *Clinical Cancer Research*, 7(3 Supp):S856-S864.

Xu et al., (1994), "Residue at Position 331 in the IgG1 and IgG4 CH2 Domains Contributes to Their Differential Ability to Bind and Activate Complement," *J. Biol. Chem.*, 269(5):3469-3474.

Yu et al., (1998), "Phase I Trial of a Human-Mouse Chimeric Anti-Disaloganglioside Monoclonal Antibody ch 14.18 in Patients with Refractory Neuroblastoma and Osteosarcoma," *J. Clinical Oncology*, 16(6):2169-80.

Anderson et al., (1980), "Characterization of the Fc Receptor for IgG on a Human Macrophage Cell Line U937," *J. Immunol.*, 125(6):2735-41.

Anderson et al., (1994), "Effects of Route and Formulation on Clinical Pharmacokinetics of Interleukin-2," *Clin. Pharmacokinet.*, 27(1):19-31.

Baici et al., (1980), "Kinetics of the Different Susceptibilities of the Four Human Immunoglobulin G Subclasses to Proteolysis by Human Lysosomal Elastase," *Scand. J. Immunol.* 12(1):41-50.

Barbulescu et al., (1998), "IL-12 and IL-18 Differentially Regulate the Transcriptional Activity of the Human IFN-γ Promoter in Primary CD4+ T Lymphocytes," *J. Immunol.*, 160:3642-7.

Boulianne et al., (1984), "Production of Functional Chimaeric Mouse/Human Antibody," *Nature*, 312:643-6.

Bourgois et al., (1974), "Determination of the Primary Structure of a Mouse IgG2a Immunoglobulin: Amino-Acid Sequence of the Fc Fragment: Implications for the Evolution of Immunoglobulin Structure and Function," *Eur. J. Biochem.*, 43:423-35.

Brambell et al., (1964), "A Theoretical Model of γ-Globulin Catabolism," *Nature*, 203:1352-55.

Brekke et al., (1994), "Human IgG Isotype-Specific Amino Acid Residues Affecting Complement-Mediated Cell Lysis and Phagocytosis," *Eur. J. Immunol.*, 24:2542-2547.

Bubenik et al., (1995) "Interleukin-2 Gene Therapy of Residual EL-4 Leukaemia Potentiates the Effect of Cyclophosphamide Pretreatment," *J. Cancer Res. Clin. Oncol.*, 121:39-43.

Chan et al., (1992), "Mechanisms of IFN-γ Induction by Natural Killer Cell Stiumlatory Factor (NKSF/IL-12). Role of Transcription and mRNA Stability in the Synergistic Interaction Between NKSF and IL-2," *J. Immunol.*, 148:92-98.

Chapman et al., (1994), "Mapping Effector Functions of a Monoclonal Antibody to GD3 by Characterization of a Mouse-Human Chimeric Antibody," *Cancer Immuno. Immunother.*, 39:198-204.

Chappel et al., (1991), "Identification of the Fc Gamma Receptor Class 1 Binding Site in Human IgG Through Use of Recombinant IgG1/IgG2 Hybrid and Point-Mutated Antibodies," *Proc. Natl. Acad. Sci. USA*, 88(20):9036-40.

Cirulli et al., (1998), "KSA Antigen Ep-CAM Mediates Cell-Cell Adhesion of Pancreatic Epithelial Cells: Morphoregulatory Roles in Pancreatic Islet Development," *J. Cell Biol.*, 140:1519-34.

Cohen et al., (1998), "An Artificial Cell-Cycle Inhibitor Isolated from a Combinatorial Library," *Proc. Natl. Acad. Sci. USA*, 95:14272-7.

Connor et al., (2004), "Ex vivo Evaluation of Anti-EpCAM Immunocytokine huKS-IL2 in Ovarian Cancer," *J. Immunotherapy*, 27:211-219.

Cosenza et al., (1997), "Disulfide Bond Assignment in Human Interleukin-7 by Matrix-Assisted Laser Desorption/Ionization Mass Spectroscopy and Site-Directed Cysteine to Serine Mutational Analysis," *J. Biol. Chem.*, 272:32995-3000.

de la Salle et al., (1996), "FcγR on Human Dendritic Cells," in *Human IgG Receptors*, pp. 39-55, van de Winkel et al. (eds.), R.G. Landes Co.

Desai et al., (1992), "IL-12 Receptor. II. Distribution and Regulation of Receptor Expression," *J. Immunol.*, 148:3125-32.

Dorai et al., (1991), "Aglycosylated Chimeric Mouse/Human IgG1 Antibody Retains Some Effector Function," *Hybridoma*, 10(2):211-217.

Dorai et al., (1992), "Role of Inter-Heavy and Light Chain Disulfide Bonds in the Effector Functions of Human IgG1," *Molecular Immunology*, 29(12):1487-1491.

Ellison et al., (1982), "The Nucleotide Sequence of a Human Immunoglobulin C γ$_1$ Gene," *Nucleic Acids Res.*, 10:4071-9.

Farner et al., (1995), "Distinction Between γ$_c$ C Detection and Function in YT Lymphoid Cells and in the Granulocyte-Macrophage Colony-Stimulating Factor-Responsive Human Myeloid Cell Line, Tf-1," *Blood*, 86:4568-78.

Ghetie et al., (1997), "FcRn: The MHC Class I-Related Receptor that is More Than an IgG Transporter," *Immunology Today*, 18(12):592-598.

Gillies et al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/Recombinant Antibody," *J. Immunology*, 146(3):1067-1071.

Gurewich et al., (1988), "Charcterization of the Intrinsic Fibrinolytic Properties of Pro-Urokinase Through a Study of Plasmin-Resistant Mutant Forms Produced by Site-Specific Mutagenesis of Lysine," *J. Clin. Invest.*, 82:1956-1962.

Handgretinger et al., (1995), "A Phase I Study of Human/Mouse Chimeric Anti-Ganglioside GD2 Antibody ch14.18 in Patients with Neuroblastoma," *European J. Cancer*, 31A(2):261-267.

Hashimoto et al., (1999), "Differential Antitumor Effects of Administration of Recombinant IL-18 or Recombinant IL-12 are Mediated Primarily by Fas-Fas Ligand- and Perforin-Induced Tumor Apoptosis, Respectively," *J. Immunol.*, 163:583-9.

Hori et al., (1987), "Establishment of an Interleukin 2-Dependent Human T Cell Line from a Patient with T Cell Chronic Lymphocytic Leukemia Who is Not Infected with Human T Cell Leukemia/Lymphoma Virus," *Blood*, 70:1069-72.

Hulett et al., (1994), "Molecular Basis of Fc Receptor Function," *Adv. Immunol.*, 57:1127.

Hurn, et al., (1980), "Production of Reagent Antibodies," *Methods in Enzymology*, 70: 104-142.

Huston et al., (1988), "Protein Engineering of Antibody Binding Sites: Recovery of Specific Activity in an Anti-Digoxin Single-Chain Fv Analogue Produced in *Escherichia Coli*," *Proc. Natl. Sci. USA*, 85:5879-5883.

Isaacs et al., (1998), "Therapy with Monoclonal Antibodies. II. The Contribution of Fcγ Receptor Binding and the Influence of CH1 and CH3 Domains on In Vivo Effector Funcion," *J. Immunol.*, 161:3862-3869.

Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," *J. Immunology*, 114(6):1726-1729.

Jefferis et al., (1990), "Molcular Definition of Interaction Sites on Human IgG for Fc Receptors huFcγR," *Mol. Immunol.*, 27(12):1237-1240.

Kelner et al., (1994), "Lymphotactin: A Cytokine that Represents a New Class of Chemokine," *Science*, 266:1395-9.

King et al., (2004), "Phase I Clinical Trial of the Immunocytokine EMD 273063 in Melanoma Patients," *J. Clin. Oncol.*, 22(22):4463-73.

Kirkman et al., (1989), "Prolongation of Cardiac Allograft Survival in Murine Recipients Treated with a Diphtheria Toxin-Related Interleukin-2 Fusion Protein," *Transplantation*, 47(2):327-330.

Ko et al., (2004), "Safety, Pharmacokinetics, and Biological Pharmacodynamics of the Immunocytokine EMD 273066 (huKS-IL2)," *J. Immunotherapy*, 27:232-239.

Lanza et al., (1993), "Active Immunity against the CD4 Receptor by Using an Antibody Antigenized with Residues 41-55 of the First Extracellular Domain," *Proc. Natl. Acad. Sci. USA*, 90:11683-7.

Lo et al., (1992), "Expression and Secretion of an Assembled Tetrameric CH2-Deleted Antibody in *E. coli*.," *Hum. Antibod. Hybridomas*, 3:123-128.

Lode et al., (1998), "Gene Therapy with a Single Chain Interleukin 12 Fusion Protein Induces T Cell-Dependent Protective Immunity in a Syngeneic Model of Murine Neuroblastoma," *Proc. Natl. Acad. Sci. USA*, 95:2475-80.

Lotze et al., (1996), "Cytokine Gene Therapy of Cancer Using Interleukin-12: Murine and Clinical Trials," *Ann. NY Acad. Sci.*, 795:440-54.

MacLean et al., (1996), "Enhancing the Effect of Theratope STn-KLH Cancer Vaccine in Patients with Metastatic Breast Cancer by Pretreatment with Low-Dose Intravenous Cyclophosphamide," *J. Immunother.*, 19(4):309-316.

Maghazachi et al., (1997), "Interferon-Inducible Protein-10 and Lymphotactin Induce the Chemotaxis and Mobilization of Intracellular Calcium in Natural Killer Cells through Pertussis Toxin-Sensitive and -Insensitive Heterotrimeric G-Proteins," *FASEB J.*, 11:765-74.

Mariani et al., (1997), "Tumor Targeting Potential of the Monoclonal Antibody BC-1 against Oncofetal Fibronectin in Nude Mice Bearing Human Tumor Implants," *Cancer*, 80:2378-84.

Martin et al., (2001), "Crystal Structure at 2.8 Å of an FcRn/Heterodimeric Fc Complex: Mechanism of pH-Dependent Binding," *Mol. Cell.*, 7(4):867-77.

McMahan et al., (1991), "A Novel IL-1 Receptor, Cloned From B-Cells by Mammalian Expression is Expressed in Many Cell Types," *EMBO J.*, 10:2821-32.

Mehrotra et al., (1993), "Effects of IL-12 on the Generation of Cytotoxic Activity in Human CD8+ T Lymphocytes" *J. Immunol.*, 151:2444-52.

Menard et al., (1983), "Generation of Monoclonal Antibodies Reacting with Normal and Cancer Cells of Human Breast," *Cancer Res.*, 43:1295-300.

Miyake et al., (1988), "Synthesis of Recombinant Human Single-Chain Urokinase-Type Plasminogen Activator Variants Resistant to Plasmin and Thrombin," *J. Biochem.*, 104:643-647.

Morrison et al., (1984), "Chimeric Human Antibody Molecules: Mouse Antigen-Binding Domains with Human Constant Region Domains," *Proc. Natl. Acad. Sci. USA*, 81:6851-5.

Mueller et al., (1990), "Enhancement of Antibody-Dependent Cytotoxicity With A Chimeric Anti-GD2 Antibody," *J. Immunology*, 144(4):1382-1386.

Mueller et al., (1990), "Serum Half-Life and Tumor Localization of a Chimeric Antibody Deleted of the CH2 Domain and Directed Against the Disialoganglioside GD2," *Proc. Natl. Acad. Sci. USA*, 87:5702-5705.

Naramura et al., (1993), "Therapeutic Potential of Chimeric and Murine Anti-(Epidermal Growth Factor Receptor) Antibodies in a Metastasis Model for Human Melanoma," *Cancer Immuno. Immunother.*, 37:343-349.

Nastala et al., (1994), "Recombinant IL-12 Administration Induces Tumor Regression in Association with IFN-γ Production," *J. Immunol.*, 153:1697-706.

Nelles et al., (1987), "Characterization of Recombinant Human Single Chain Urokinase-Type Plaminogen Activtor Mutants Produced by Site-Specific Mutagenesis of Lysine 158," *J. Biol. Chem.*, 262(12):5682-5689.

Orlandi et al., (1989), "Cloning Immunoglobulin Variable Domains for Expression by the Polymerase Chain Reaction," *Proc. Natl. Acad. Sci. USA*, 86:3833-7.

Palucka et al., (1998), "Dendritic Cells as the Terminal Stage of Monocyte Differentiation," *J. Immunol.*, 160:4587-95.

Pedley et al., (1999), "Enhancement of Antibody-Directed Enzyme Prodrug Therapy in Colorectal Xenografts by an Antivascular Agent," *Cancer Res.*, 59:3998-4003.

Perussia et al., (1992), "Natural Killer (NK) Cell Stimulatory Factor or IL-12 Has Differential Effects on the Proliferation of TCR-αβ+, TCR-γδ+ T Lymphocytes, and NK Cells," *J. Immunol.*, 149:3495-502.

Poon et al., (1995), "Structure and Function of Several Anti-Dansyl Chimeric Antibodies Formed by Domain Interchanges Between Human IgM and Mouse IgG2b," *J. Biol. Chem.*, 270:8571-7.

Queen et al., (1989), "A Humanized Antibody that Binds to the Interleukin 2 Receptor," *Proc. Natl. Acad. Sci. USA*, 86:10029-33.

Reisfeld et al., (1994), "Potential of Genetically Engineered Anti-Ganglioside GD2 Antibodies for Cancer Immunotherapy," *Prog. Brain Res.*, 101:201-212.

Riechmann et al., (1988), "Reshaping Human Antibodies for Therapy," *Nature*, 332:323-7.

Robinson et al., (1998), "Optimizing the Stability of Single-Chain Proteins by Linker Length and Composition Mutagenesis," *Proc. Natl. Acad. Sci. USA*, 95:5929-34.

Sakano et al., (1980), "Two Types of Somatic Recombination are Necessary for the Generation of Complete Immunoglobin Heavy-Chain Genes," *Nature*, 286:676-683.

Saleh et al., (1992), "Phase I Trial of the Chimeric Anti-GD2 Monoclonal Antibody ch14.18 in Patients With Malignant Melanoma," *Hum. Antiob. Hybridomas*, 3:19-24.

Schlom (1991), "Monoclonal Antibodies: They're More and Less Than You Think," in *Molecular Foundations of Oncology*, pp. 95-133.

Senior et al., (2000), "Cleavage of a Recombinant Human Immunoglobulin A2 (igA2)-IgA1 Hybrid Antibody by Certain Bacterial IgA1 Proteases," *Infect. Immun.*, 68(2):463-9.

Sharp et al., (1988), "Codon Usage Patterns in *Escherichia coli, Bacillus subtilis, Saccharomyces cerevisiae, Schizosaccharomyces pombe, Drosophila melanogaster* and *Homo sapiens*; a Review of the Considerable Within-Species Diversity," *Nucleic Acids Res.*, 16(17):8207-8211.

Takai, (2002), "Roles of Fc Receptors in Autoimmunity," *Nat. Rev. Immunol.*, 2(8):580-92.

Thurner, (1999), "Generation of Large Numbers of Fully Mature and Stable Dendritic Cells from Leukapheresis Products for Clinical Application," *J. Immunol. Methods*, 223:1-15.

Tiruppathi et al., (1996), "Isolation and Characterization of a Cell Surface Albumin-Binding Protein from Vascular Endothelial Cells," *Proc. Nat. Acad. Sci. USA*, 93:250-4.

Voest et al., (1995), "Inhibition of Angiogenesis in Vivo by Interleukin 12," *J. Natl. Canc. Inst..*, 87:581-6.

Ward et al., (1995), "The Effector Functions of Immunoglobulins: Implications for Therapy," *Therapeutic Immunology*, 2:77-94.

Weber et al., (2001), "Phase I Trial of huKS-IL2 Immunocytokine in Patients with Prostate Carcinoma: Clinical, PK, and Biological PD Results (Abstract)," *American Society of Clinical Oncology Program/Proceedings*, 20(Part 1):259a.

Weitkamp et al., (1973), "Additional Data on the Population Distribution of Human Serum Albumin Genes; Three New Variants," *Ann. Hum. Genet.*, 37:219-26.

Wetzel et al., (2001), "BAY50-4798, an Interleukin-2 (IL-2) Variant, Demonstrates Selective Activation of Human and Chimpanzee T Cells Relative to NK Cells but Shows Less Selectivity for T Cells from Monkeys and Rodents," *ASCO 2001 Annual Meeting*, Abstract #1051.

Woof et al., (1986), "Localisation of the Monocyte-Binding Region on Human Immunoglobulin G," *Mol. Immunol.*, 23:319-30.

Wysocka et al., (1995), "Interleukin-12 is Required for Interferon-γ Production and Lethality in Lipoplysaccharide-Induced Shock in Mice," *Eur. J. Immunol.*, 25:672-6.

Yan et al., (1996), "Charcterization of an Ig VH Idiotope that Results in Specific Homophilic Binding and Increased Avidity for Antigen," *J. Immunol.*, 157:1582-8.

Yeh et al., (1992), "Design of Yeast-Secreted Albumin Derivatives for Human Therapy: Biological and Antiviral Properties of a Serum Albumin-CD4 Genetic Conjugate," *Proc. Natl. Acad. Sci. USA*, 89:1904-8.

Zhu et al., (2001), "MHC Class I-Related Neonatal Fc Receptor for IgG is Functionally Expressed in Monocytes, Intestinal Macrophages andn Dendritic Cells," *J. Immunol.*, 166:3266-3276.

Zuckier et al., (1998), "Chimeric Human-Mouse IgG Antibodies with Shuffled Constant Region Exons Demonstrate that Multiple Domains Contribute to In Vivo Half-Life," *Cancer Res.*, 58(17):3905-8.

* cited by examiner though this approach has been demonstrated in several mouse tumor metastasis models, however, treatment is far less effective as the size of the tumors increases. This is likely due to the increased level of suppressive factors secreted by the tumor mass as well as other factors, such as the increase in tumor interstitial fluid pressure (Griffon-Etienne et al. 1999, CANCER RES. 59:3776-3782), a barrier to penetration of solid tumors by therapeutic agents.

ENHANCEMENT OF ANTIBODY-CYTOKINE FUSION PROTEIN MEDIATED IMMUNE RESPONSES BY COMBINED TREATMENT WITH IMMUNOCYTOKINE UPTAKE ENHANCING AGENTS

RELATED APPLICATIONS

This application claims priority to, and the benefit of 60/215,038 filed Jun. 29, 2000, the disclosure of which is incorporated by reference herein.

FIELD OF THE INVENTION

The present invention relates to antibody-cytokine fusion proteins useful for targeted immune therapy. In general, the invention relates to the use of immunocytokine uptake enhancing agents in combination therapy to enhance an antibody-cytokine fusion protein mediated immune response against a preselected target, for example, cells in a tumor. In particular, the invention relates to the administration of antibody-cytokine fusion proteins in combination with chemotherapeutics such as taxanes and/or alkylating agents to treat tumor cells and other cancerous or diseased cells.

BACKGROUND OF THE INVENTION

Effective treatment of diseases such as cancer require robust immune responses by one or more effector cell types such as natural killer (NK) cells, macrophage and T lymphocytes. In animals and patients bearing tumors, the immune system has not effectively dealt with the growing tumor due, in large part, to specific mechanisms the tumor has elaborated to suppress the immune response. In many cases, potentially tumor-destructive monocytic cells, e.g. macrophages, migrate into growing tumor beds, but the secretion of factors such as prostaglandins, TGF-β and IL-10 by the tumor cells modulate their cytotoxic activity (see, for example, Sharma et al., 1999, J. IMMUNOL. 163:5020-5028). Likewise, lymphocytic cells migrating into tumors, such as NK and T cells, can be suppressed by factors secreted by tumors as well as by interactions with receptors expressed on the surface of tumor cells that activate apoptosis of the immune cells (see, for example, Villunger, et al, 1997, BLOOD 90:12-20). The exposure of these lymphocytes to immunosuppressive monocytic cells within the tumor bed can further reduce their ability to mount an effective anti-tumor response.

Efforts made to overcome the immune suppressive effects of the local tumor microenvironment include targeted immune stimulation, such as treatment with tumor-specific antibody-cytokine fusion proteins. Effective treatment with this approach has been demonstrated in several mouse tumor metastasis models, however, treatment is far less effective as the size of the tumors increases. This is likely due to the increased level of suppressive factors secreted by the tumor mass as well as other factors, such as the increase in tumor interstitial fluid pressure (Griffon-Etienne et al. 1999, CANCER RES. 59:3776-3782), a barrier to penetration of solid tumors by therapeutic agents.

While most cancer patients are still treated with one or more courses of chemotherapy, it is well known that cytotoxic therapy of cancer is damaging to the immune system. Immune cells are among the most rapidly dividing cells in the human body, and any treatment that kills dividing cells will also kill immune cells. Thus, treatments including radiation, DNA-damaging chemicals, inhibitors of DNA synthesis, and inhibitors of microtubule function all cause damage to the immune system. Bone marrow transplants are needed as an adjunct to cancer therapy precisely because the immune system becomes damaged and needs to be replenished. Methotrexate and other anti-cancer drugs are often used as immunosuppressants. There is also evidence that anti-cancer treatments can specifically inhibit T cell function. For example, patients who have been treated for Hodgkin's disease with whole-body irradiation suffer from an apparently permanent loss of naïve T cells (Watanabe et al., 1997, Blood 90:3662).

Based on current knowledge it would appear unlikely that standard treatments (chemotherapy and radiation) and local immune stimulation would be a useful combination approach for effective treatment of cancer. Therefore, there is a need in the art for methods that enhance antibody-cytokine fusion protein mediated immune responses against pre-selected cell types, for example, tumor cells, and compositions employed in such methods.

SUMMARY OF THE INVENTION

It has been discovered that when an antibody-cytokine fusion protein (immunocytokine) is administered to a mammal bearing a tumor or tumor metastases, it is possible to create a more potent anti-tumor response if it is administered before, simultaneously with, or after treatment of the mammal with an immunocytokine uptake enhancing agent that increases or enhances the therapeutic effect of the antibody-cytokine fusion protein by enhancing or increasing its uptake by the tumor. It has been found that useful immunocytokine uptake enhancing agents comprise alkylating chemotherapeutic agents and taxanes such as paclitaxel. In particular, it has been found that such combinations are useful in mediating the immune destruction of the pre-selected cell type, such as tumor cells or virus-infected cells.

In one aspect, the invention provides a method of inducing a cytocidal immune response against a preselected cell-type in a mammal. The method comprises administering to the mammal (i) an immunocytokine comprising an antibody binding site capable of binding the preselected cell-type and a cytokine capable of inducing such an immune response against the preselected cell-type, and (ii) an immunocytokine uptake enhancing agent in an amount sufficient to enhance the immune response relative to the immune response stimulated by the immunocytokine alone.

In a preferred embodiment, the preselected cell-type can be a cancer cell present, for example, in a solid tumor, more preferably in a larger, solid tumor (i.e., greater than about 100 mm$^3$). Alternatively, the preselected cell-type can be a cancer cell present in the form of small metastases.

In another preferred embodiment, the immunocytokine uptake enhancing agent can be administered simultaneously with the immunocytokine. Alternatively, the immunocytokine uptake enhancing agent can be administered prior to administration of the immunocytokine. Furthermore, it is contemplated that the immunocytokine can be administered together with a plurality of different immunocytokine uptake enhancing agents. Alternatively, it is contemplated that an immunocytokine uptake enhancing agent can be administered together with a plurality of different immunocytokines.

In another aspect, the invention provides a composition for inducing a cytocidal immune response against a preselected cell-type in a mammal. The composition comprises in combination: (i) an immunocytokine comprising an antibody binding site capable of binding the preselected cell-type, and a cytokine capable of inducing such an immune response against the preselected cell-type in the mammal, and (ii) an immunocytokine uptake enhancing agent in an amount sufficient to enhance the cytocidal response induced by the immunocytokine of the combination relative to the cytocidal response stimulated by the immunocytokine alone.

In a preferred embodiment, the antibody binding site of the immunocytokine preferably comprises an immunoglobulin heavy chain or an antigen binding fragment thereof. The immunoglobulin heavy chain preferably comprises, in an amino-terminal to carboxy-terminal direction, an immunoglobulin variable ($V_H$) region domain capable of binding a preselected antigen, an immunoglobulin constant heavy 1 (CH1) domain, an immunoglobulin constant heavy 2 (CH2) domain, and optionally may further include an immunoglobulin constant heavy 3 (CH3) domain. In a more preferred embodiment, the immunocytokine is a fusion protein comprising an immunoglobulin heavy chain or an antigen binding fragment thereof fused via a polypeptide bond to the cytokine. Accordingly, a preferred antibody-cytokine fusion protein comprises, in an amino-terminal to carboxy-terminal direction, (i) the antibody binding site comprising an immunoglobulin variable region capable of binding a cell surface antigen on the preselected cell-type, an immunoglobulin CH1 domain, an immunoglobulin CH2 domain (optionally a CH3 domain), and (ii) the cytokine. Methods for making and using such fusion proteins are described in detail in Gillies et al. (1992) Proc. Natl. Acad. Sci. USA 89: 1428-1432; Gillies et al. (1998) J. Immunol. 160: 6195-6203; and U.S. Pat. No. 5,650,150.

The immunoglobulin constant region domains (i.e., the CH1, CH2 and/or CH3 domains) may be the constant region domains normally associated with the variable region domain in a naturally occurring antibody. Alternatively, one or more of the immunoglobulin constant region domains may be derived from antibodies different from the antibody used as a source of the variable region domain. In other words, the immunoglobulin variable and constant region domains may be derived from different antibodies, for example, antibodies derived from different species. See, for example, U.S. Pat. No. 4,816,567. Furthermore, the immunoglobulin variable regions may comprise framework region (FR) sequences derived from one species, for example, a human, and complementarity determining region (CDR) sequences interposed between the FRs, derived from a second, different species, for example, a mouse. Methods for making and using such chimeric immunoglobulin variable regions are disclosed, for example, in U.S. Pat. Nos. 5,225,539 and 5,585,089.

The antibody-based immunocytokines preferably further comprise an immunoglobulin light chain which preferably is covalently bonded to the immunoglobulin heavy chain by means of, for example, a disulfide bond. The variable regions of the linked immunoglobulin heavy and light chains together define a single and complete binding site for binding the preselected antigen. In other embodiments, the immunocytokines comprise two chimeric chains, each comprising at least a portion of an immunoglobulin heavy chain fused to a cytokine. The two chimeric chains preferably are covalently linked together by, for example, one or more interchain disulfide bonds.

The invention thus provides fusion proteins in which the antigen-binding specificity and activity of an antibody is combined with the potent biological activity of a cytokine. A fusion protein of the present invention can be used to deliver the cytokine selectively to a target cell in vivo so that the cytokine can exert a localized biological effect in the vicinity of the target cell. In a preferred embodiment, the antibody component of the fusion protein specifically binds an antigen on or within a cancer cell and, as a result, the fusion protein exerts localized anti-cancer activity. In an alternative preferred embodiment, the antibody component of the fusion protein specifically binds a virus-infected cell, such as an HIV-infected cell, and, as a result, the fusion protein exerts localized anti-viral activity.

Cytokines that can be incorporated into the immunocytokines of the invention include, for example, tumor necrosis factors, interleukins, colony stimulating factors, and lymphokines, as well as others known in the art. Preferred tumor necrosis factors include, for example, tissue necrosis factor α (TNFα). Preferred interleukins include, for example, interleukin-2 (IL-2), interleukin-4 (IL-4), interleukin-5 (IL-5), interleukin-7 (IL-7), interleukin-12 (IL-12), interleukin-15 (IL-15) and interleukin-18 (IL-18). Preferred colony stimulating factors include, for example, granulocyte-macrophage colony stimulating factor (GM-CSF) and macrophage colony stimulation factor (M-CSF). Preferred lymphokines include, for example, lymphotoxin (LT). Other useful cytokines include interferons, including IFN-α, IFN-β and IFN-γ, all of which have immunological effects, as well as anti-angiogenic effects, that are independent of their anti-viral activities.

It has been found that several types of chemotherapeutic agents are effective immunocytokine uptake enhancing agents. In particular, useful immunocytokine uptake enhancing agents include taxanes and alkylating chemotherapeutic agents. Several taxanes are known in the art (see Bissery and Lavelle, 1997, in *Cancer Therapeutics: Experimental and Clinical Agents*, Chapter 8, B. Teicher, ed.). In a preferred embodiment, the taxane is Taxol, also known as paclitaxel. Other embodiments include the semisynthetic taxane, docetaxel, which in some tumor models and clinical indications is more efficacious than paclitaxel. Further embodiments include additional taxane derivatives, such as those derived from the natural starting material, 10-deacetyl Baccatin III, extracted from the needles of the European Yew tree. One such example is the orally available compound, IDN5109, which is also a poor substrate for P-glycoprotein and generally more active against multidrug resistant tumors. In addition to being orally bioavailable, it also has a higher tolerated dose and exhibits less neurotoxic side effects (Polizzi et al., 1999, Cancer Res. 59:1036-1040).

Also provided are preferred dosages and administration regimes for administering the immunocytokines in combination with the immunocytokine uptake enhancing agents.

DETAILED DESCRIPTION OF THE INVENTION

Figure 1:
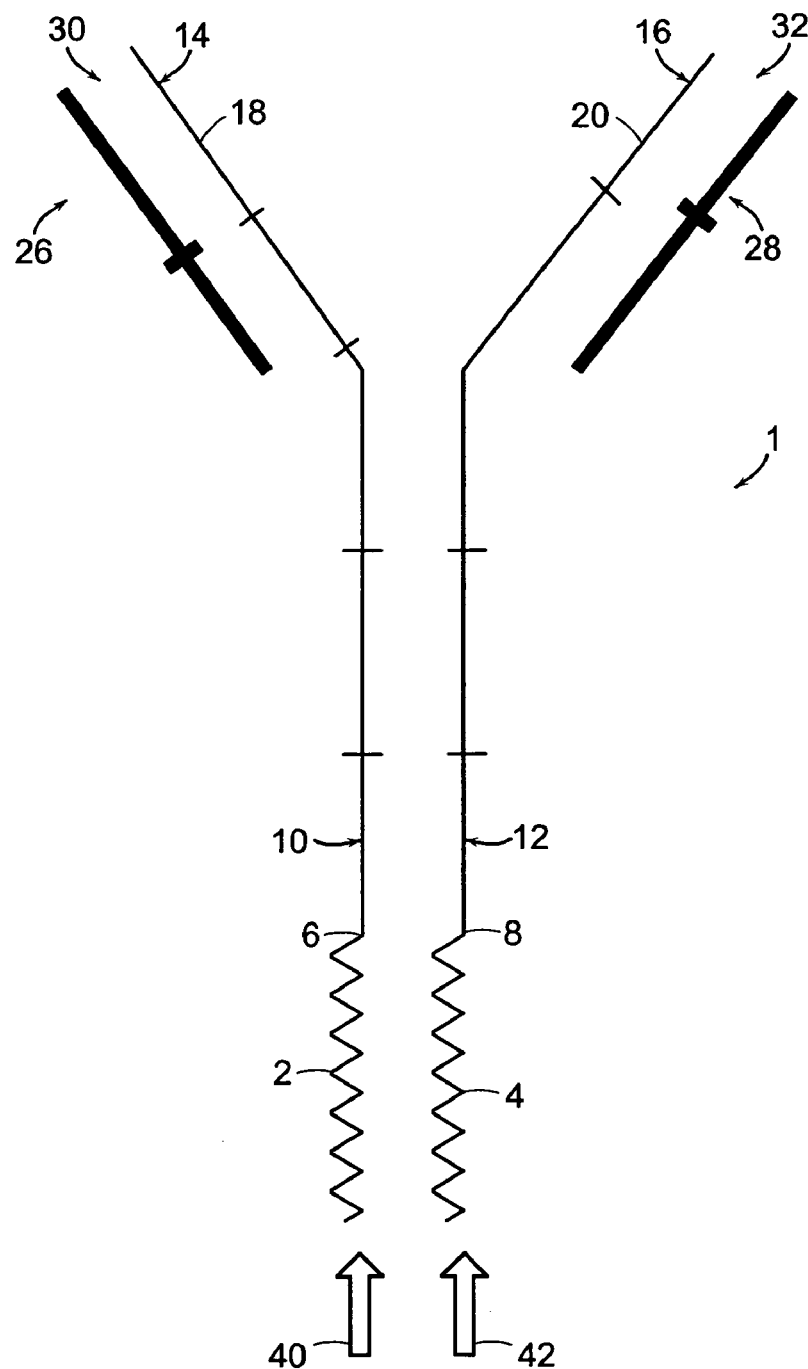
FIG. 1 is a schematic representation of a cytokine.

Studies have shown that large, solid tumors are much more refractory to antibody-mediated therapeutic intervention, and to immune therapies in general than are disseminated metastatic foci (Sulitzeanu et al. (1993) Adv. Cancer Res. 60: 247-267). It is believed that low responsiveness to antibody-based therapies is based, in part, upon the production of immunosuppressive factors by the tumors.

Although the mechanism for tumor eradication is not completely understood, it is contemplated that cytotoxic T lymphocyte (CTL) responses can lead to destruction of cancer cells and provide immune memory. Furthermore, it is contemplated that under certain circumstances natural killer (NK) cells are responsible for tumor eradication in the absence of CTLs. The different immune responses may result from the fact that certain tumors produce different types or amounts of substances capable of down-regulating T cells. This is especially true for solid tumors, rather than micrometastatic foci, that have reached a critical mass and are capable of producing and secreting immunosuppressive factors at levels sufficient to modulate an immune response against the tumors.

It has now been discovered that cytocidal immune responses initiated by an immunocytokine against a preselected cell-type can be enhanced significantly by administering the immunocytokine together with an immunocytokine uptake enhancing agent. The combined therapy is particularly effective in mediating the immune destruction of a diseased tissue, such as, an established tumor. Without wishing to be bound by theory, it is contemplated that the immunocytokine uptake enhancing agent increases the penetration of the immunocytokine into the tumor microenvironment thus making it capable of overcoming the immune suppressive effect and more effective at activating cellular immune responses against the tumor. Similarly, it is contemplated that such a method may be useful for the treatment of certain viral diseases where a similar immune suppressive mechanism prevents effective cellular immunity, for example, in HIV infection. It is contemplated that the immunocytokine uptake enhancing agent acts synergistically with the immunocytokine to mediate the immune destruction of a diseased tissue such as an established tumor or virally-infected cells. The present invention also describes methods for making and using useful immunocytokines, as well as assays useful for testing their pharmacokinetic activities in pre-clinical in vivo animal models when combined with suitable immunocytokine uptake enhancing agents.

As used herein, the term "immunocytokine uptake enhancing agent" is understood to mean any agent that enhances a cytocidal immune response induced by an immunocytokine against a pre-selected cell type. More specifically, a preferred immunocytokine uptake enhancing agent is a tumor uptake enhancing agent that increases the penetration of an immunocytokine into a tumor. Examples of immunocytokine uptake enhancing agents include, but are not limited to, chemotherapeutic agents such as taxanes, DNA damaging agents including alkylating chemotherapeutic agents, radiation therapy agents, and agents that modulate blood pressure. Preferred taxanes are taxol, docetaxel, 10-deacetyl Baccatin III, and derivatives thereof. Preferred alkylating agents are cyclophosphamide, carboplatin, cisplatin, and derivatives thereof. A preferred form of radiation is gamma irradiation. A preferred blood pressure modulating agent is an angiotensin II agonist, such as angiotensin II itself, preferably administered periodically according to the general priciples described by Netti et al. (Cancer Research [1995] 55:5451-8) and Netti et al (Proc. Nat. Acad. Sci. [1999] 96:3137-3142). Immune response may be determined by methods known to one of ordinary skill in the art and/or as described herein.

As used herein, the term "cytocidal immune response" is understood to mean any immune response in a mammal, either humoral or cellular in nature, that is stimulated by an immunocytokine and which either kills or otherwise reduces the viability of a preselected cell-type in the mammal. The immune response may include one or more cell types, including T cells, NK cells and macrophages.

As used herein, the term "immunocytokine" is understood to mean a fusion of (i) an antibody binding site having binding specificity for, and capable of binding a pre-selected antigen, for example, a cell-type specific antigen, and (ii) a cytokine that is capable of inducing or stimulating a cytocidal immune response typically against a cancer or virally-infected cell. Examples of pre-selected antigens include cell surface antigens such as on cancer cells or virally-infected cells, and insoluble intracellular antigens, for example, of necrotic cells, which can remain attached to the cell membrane. Preferred antigens are target antigens that are characteristic of tumor cells, such as tumor specific antigens. Accordingly, the immunocytokine is capable of selectively delivering the cytokine to a target (which typically is a cell) in vivo so that the cytokine can mediate a localized immune response against a target cell. For example, if the antibody component of the immunocytokine selectively binds an antigen on a cancer cell, such as a cancer cell in a solid tumor, and in particular a larger solid tumor of greater than about 100 mm$^3$, the immunocytokine exerts localized anti-cancer activity. Alternatively, if the antibody component of the immunocytokine selectively binds an antigen on a virally-infected cell, such as a HIV infected cell, the immunocytokine exerts localized anti-viral activity.

As used herein, the term "antibody binding site" is understood to mean at least a portion of an immunoglobulin heavy chain, for example, an immunoglobulin variable region capable of binding a pre-selected antigen such as a cell type. The antibody binding site also preferably comprises at least a portion of an immunoglobulin constant region including, for example, a CH1 domain, a CH2 domain, and optionally, a CH3 domain, or at least a CH2 domain, or one or more portions thereof. Furthermore, the immunoglobulin heavy chain may be associated, either covalently or non-covalently, to an immunoglobulin light chain comprising, for example, an immunoglobulin light chain variable region and optionally light chain constant region. Accordingly, it is contemplated that the antibody binding site may comprise an intact antibody or a fragment thereof, or a single chain antibody, capable of binding the preselected antigen.

With regard to the immunocytokine, it is contemplated that the antibody fragment may be linked to the cytokine by a variety of ways well known to those of ordinary skill in the art. For example, the antibody binding site preferably is linked via a polypeptide bond or linker to the cytokine in a fusion protein construct. Alternatively, the antibody binding site may be chemically coupled to the cytokine via reactive groups, for example, sulfhydryl groups, within amino acid sidechains present within the antibody binding site and the cytokine.

As used herein, the term "cytokine" is understood to mean any protein or peptide, analog or functional fragment thereof, which is capable of stimulating or inducing a cytocidal immune response against a preselected cell-type, for example, a cancer cell or a virally-infected cell, in a mammal. Accordingly, it is contemplated that a variety of cytokines can be incorporated into the immunocytokines of the invention. Useful cytokines include, for example, tumor necrosis factors (TNFs), interleukins (ILs), lymphokines (Ls), colony stimulating factors (CSFs), interferons (IFNs) including species variants, truncated analogs thereof which are capable of stimulating or inducing such cytocidal immune responses. Useful tumor necrosis factors include, for example, TNFα. Useful lymphokines include, for example, LT. Useful colony stimulating factors include, for example, GM-CSF and M-CSF. Useful interleukins include, for example, IL-2, IL-4, IL-5, IL-7, IL-12, IL-15 and IL-18. Useful interferons, include, for example, IFN-α, IFN-β and IFN-γ.

The gene encoding a particular cytokine of interest can be cloned de novo, obtained from an available source, or synthesized by standard DNA synthesis from a known nucleotide sequence. For example, the DNA sequence of LT is known (see, for example, Nedwin et al. (1985) NUCLEIC ACIDS RES. 13: 6361), as are the sequences for IL-2 (see, for example, Taniguchi et al. (1983) NATURE 302: 305-318), GM-CSF (see, for example, Gasson et al. (1984) SCIENCE 266: 1339-1342), and TNFα (see, for example, Nedwin et al. (1985) NUCLEIC ACIDS RES. 13: 6361).

In a preferred embodiment, the immunocytokines are recombinant fusion proteins produced by conventional recombinant DNA methodologies, i.e., by forming a nucleic acid construct encoding the chimeric immunocytokine. The construction of recombinant antibody-cytokine fusion proteins has been described in the prior art. See, for example, Gillies et al. (1992) Proc. Natl. Acad. Sci. USA 89: 1428-1432; Gillies et al. (1998) J. Immunol. 160: 6195-6203; and U.S. Pat. No. 5,650,150. Preferably, a gene construct encoding the immunocytokine of the invention includes, in 5' to 3' orientation, a DNA segment encoding an immunoglobulin heavy chain variable region domain, a DNA segment encoding an immunoglobulin heavy chain constant region, and a DNA encoding the cytokine. The fused gene is assembled in or inserted into an expression vector for transfection into an appropriate recipient cell where the fused gene is expressed. The hybrid polypeptide chain preferably is combined with an immunoglobulin light chain such that the immunoglobulin variable region of the heavy chain ($V_H$) and the immunoglobulin variable region of the light chain ($V_L$) combine to produce a single and complete site for binding a preselected antigen. In a preferred embodiment, the immunoglobulin heavy and light chains are covalently coupled, for example, by means of an interchain disulfide bond. Furthermore, two immunoglobulin heavy chains, either one or both of which are fused to a cytokine, can be covalently coupled, for example, by means of one or more interchain disulfide bonds.

Accordingly, methods of the invention are useful to enhance the anti-tumor activity of an immunocytokine used in a therapeutic method to treat a tumor, including immunocytokine compositions and methods disclosed in WO99/29732, WO99/43713, WO99/52562, WO99/53958, and WO01/10912, and antibody-based fusion proteins with an altered amino acid sequence in the junction region. In one embodiment, methods of the invention are useful in combination with Fc fusion proteins such as Fc-interferon-α.

FIG. 1 shows a schematic representation of an exemplary immunocytokine 1. In this embodiment, cytokine molecules 2 and 4 are peptide bonded to the carboxy termini 6 and 8 of CH3 regions 10 and 12 of antibody heavy chains 14 and 16. $V_L$ regions 26 and 28 are shown paired with $V_H$ regions 18 and 20 in a typical IgG configuration, thereby providing two antigen binding sites 30 and 32 at the amino terminal ends of immunocytokine 1 and two cytokine receptor-binding sites 40 and 42 at the carboxy ends of immunocytokine 1. Of course, in their broader aspects, the immunocytokines need not be paired as illustrated or only one of the two immunoglobulin heavy chains need be fused to a cytokine molecule.

Immunocytokines of the invention may be considered chimeric by virtue of two aspects of their structure. First, the immunocytokine is chimeric in that it includes an immunoglobulin heavy chain having antigen binding specificity linked to a given cytokine. Second, an immunocytokine of the invention may be chimeric in the sense that it includes an immunoglobulin variable region (V) and an immunoglobulin constant region (C), both of which are derived from different antibodies such that the resulting protein is a V/C chimera. For example, the variable and constant regions may be derived from naturally occurring antibody molecules isolatable from different species. See, for example, U.S. Pat. No. 4,816,567. Also embraced are constructs in which either or both of the immunoglobulin variable regions comprise framework region (FR) sequences and complementarity determining region (CDR) sequences derived from different species. Such constructs are disclosed, for example, in Jones et al. (1986) Nature 321: 522-525, Verhoyen et al. (1988) SCIENCE 239: 1534-1535, and U.S. Pat. Nos. 5,225,539 and 5,585,089. Furthermore, it is contemplated that the variable region sequences may be derived by screening libraries, for example, phage display libraries, for variable region sequences that bind a preselected antigen with a desired affinity. Methods for making and screening phage display libraries are disclosed, for example, in Huse et al. (1989) Science 246: 1275-1281 and Kang et al. (1991) Proc. Natl. Acad. Sci. USA 88: 11120-11123.

The immunoglobulin heavy chain constant region domains of the immunocytokines can be selected from any of the five immunoglobulin classes referred to as IgA (Igα), IgD (Igδ), IgE (Igε), IgG (Igγ), and IgM (Igμ). However, immunoglobulin heavy chain constant regions from the IgG class are preferred. Furthermore, it is contemplated that the immunoglobulin heavy chains may be derived from any of the IgG antibody subclasses referred to in the art as IgG1, IgG2, IgG3 and IgG4. As is known, each immunoglobulin heavy chain constant region comprises four or five domains. The domains are named sequentially as follows: CH1-hinge-CH2-CH3-(-CH4). CH4 is present in IgM, which has no hinge region. The DNA sequences of the heavy chain domains have cross homology among the immunoglobulin classes, for example, the CH2 domain of IgG is homologous to the CH2 domain of IgA and IgD, and to the CH3 domain of IgM and IgE. The immunoglobulin light chains can have either a kappa (κ) or lambda (λ) constant chain. Sequences and sequence alignments of these immunoglobulin regions are well known in the art (see, for example, Kabat et al., "*Sequences of Proteins of Immunological Interest*," U.S. Department of Health and Human Services, third edition 1983, fourth edition 1987, and Huck et al. (1986) Nuc. ACIDS RES. 14: 1779-1789).

In preferred embodiments, the variable region is derived from an antibody specific for a preselected cell surface antigen (an antigen associated with a diseased cell such as a cancer cell or virally-infected cell), and the constant region includes CH1, and CH2 (and optionally CH3) domains from an antibody that is the same or different from the antibody that is the source of the variable region. In the practice of this invention, the antibody portion of the immunocytokine preferably is non-immunogenic or is weakly immunogenic in the intended recipient. Accordingly, the antibody portion, as much as possible, preferably is derived from the same species as the intended recipient. For example, if the immunocytokine is to be administered to humans, the constant region domains preferably are of human origin. See, for example, U.S. Pat. No. 4,816,567. Furthermore, when the immunoglobulin variable region is derived from a species other than the intended recipient, for example, when the variable region sequences are of murine origin and the intended recipient is a human, then the variable region preferably comprises human FR sequences with murine CDR sequences interposed between the FR sequences to produce a chimeric variable region that has binding specificity for a preselected antigen but yet while minimizing immunoreactivity in the intended host. The design and synthesis of such chimeric variable regions are disclosed in Jones et al. (1986) Nature 321: 522-525, Verhoyen et al. (1988) SCIENCE 239: 1534-1535, and U.S. Pat. Nos. 5,225,539 and 5,585,089. The cloning and expression of a humanized antibody-cytokine fusion protein, KS-1/4 anti-EpCAM antibody -IL-12 fusion protein, as well as its ability to eradicate established colon carcinoma metastases has been described in Gillies et al. (1998) J. Immunol. 160: 6195-6203.

The gene encoding the cytokine is joined, either directly or by means of a linker, for example, by means of DNA encoding a $(Gly_4-Ser)_3$ (SEQ ID NO: 15) linker in frame to the 3' end of the gene encoding the immunoglobulin constant region (e.g., a CH2 or CH3 exon). In certain embodiments, the linker can comprise a nucleotide sequence encoding a proteolytic cleavage site. This site, when interposed between the immunoglobulin constant region and the cytokine, can be designed to provide for proteolytic release of the cytokine at the target site. For example, it is well known that plasmin and trypsin cleave after lysine and arginine residues at sites that are accessible to the proteases. Many other site-specific endoproteases and the amino acid sequences they cleave are well-known in the art. Preferred proteolytic cleavage sites and proteolytic enzymes that are reactive with such cleavage sites are disclosed in U.S. Pat. Nos. 5,541,087 and 5,726,044.

The nucleic acid construct optionally can include the endogenous promoter and enhancer for the variable region-encoding gene to regulate expression of the chimeric immunoglobulin chain. For example, the variable region encoding genes can be obtained as DNA fragments comprising the leader peptide, the VJ gene (functionally rearranged variable (V) regions with joining (J) segment) for the light chain, or VDJ gene for the heavy chain, and the endogenous promoter and enhancer for these genes. Alternatively, the gene encoding the variable region can be obtained apart from endogenous regulatory elements and used in an expression vector which provides these elements.

Variable region genes can be obtained by standard DNA cloning procedures from cells that produce the desired antibody. Screening of the genomic library for a specific functionally rearranged variable region can be accomplished with the use of appropriate DNA probes such as DNA segments containing the J region DNA sequence and sequences downstream. Identification and confirmation of correct clones is achieved by sequencing the cloned genes and comparison of the sequence to the corresponding sequence of the full length, properly spliced mRNA.

The target antigen can be a cell surface antigen of a tumor or cancer cell, a virus-infected cell or another diseased cell. The target antigen may also be an insoluble intracellular antigen of a necrotic cell. (see, for example, U.S. Pat. No. 5,019,368) Genes encoding appropriate variable regions can be obtained generally from immunoglobulin-producing lymphoid cell lines, For example, hybridoma cell lines producing immunoglobulin specific for tumor associated antigens or viral antigens can be produced by standard somatic cell hybridization techniques well known in the art (see, for example. U.S. Pat. No. 4,196,265). These immunoglobulin producing cell lines provide the source of variable region genes in functionally rearranged form. The variable region genes typically will be of murine origin because this murine system lends itself to the production of a wide variety of immunoglobulins of desired specificity. Furthermore, variable region sequences may be derived by screening libraries, for example, phage display libraries, for variable region sequences that bind a preselected antigen with a desired affinity. Methods for making and screening phage display libraries are disclosed, for example, in Huse et al. (1989) Science 246: 1275-1281 and Kang et al (1991) Proc. Natl. Acad. Sci. USA 88: 11120-11123.

The DNA fragment encoding the functionally active variable region gene is linked to a DNA fragment containing the gene encoding the desired constant region (or a portion thereof). Immunoglobulin constant regions (heavy and light chain) can be obtained from antibody-producing cells by standard gene cloning techniques. Genes for the two classes of human light chains ($\kappa$ and $\lambda$) and the five classes of human heavy chains ($\alpha$, $\delta$, $\epsilon$, $\gamma$ and $\mu$) have been cloned, and thus, constant regions of human origin are readily available from these clones.

The fused gene encoding the hybrid immunoglobulin heavy chain is assembled or inserted into an expression vector for incorporation into a recipient cell. The introduction of the gene construct into plasmid vectors can be accomplished by standard gene splicing procedures. The chimeric immunoglobulin heavy chain can be co-expressed in the same cell with a corresponding immunoglobulin light chain so that a complete immunoglobulin can be expressed and assembled simultaneously. For this purpose, the heavy and light chain constructs can be placed in the same or separate vectors.

Recipient cell lines are generally lymphoid cells. The preferred recipient cell is a myeloma (or hybridoma). Myelomas can synthesize, assemble, and secrete immunoglobulins encoded by transfected genes and they can glycosylate proteins. Particularly preferred recipient or host cells include Sp2/0 myeloma which normally does not produce endogenous immunoglobulin, and mouse myeloma NS/0 cells. When transfected, the cell produces only immunoglobulin encoded by the transfected gene constructs. Transfected myelomas can be grown in culture or in the peritoneum of mice where secreted immunocytokine can be recovered from ascites fluid. Other lymphoid cells such as B lymphocytes can be used as recipient cells.

There are several methods for transfecting lymphoid cells with vectors containing the nucleic acid constructs encoding the chimeric immunoglobulin chain. For example, vectors may be introduced into lymphoid cells by spheroblast fusion (see, for example, Gillies et al. (1989) BIOTECHNOL. 7: 798-804). Other useful methods include electroporation or calcium phosphate precipitation (see, for example, Sambrook et al. eds (1989) "*Molecular Cloning: A Laboratory Manual*," Cold Spring Harbor Press).

Other useful methods of producing the immunocytokines include the preparation of an RNA sequence encoding the construct and its translation in an appropriate in vivo or in vitro expression system. It is contemplated that the recombinant DNA methodologies for synthesizing genes encoding antibody-cytokine fusion proteins, for introducing the genes into host cells, for expressing the genes in the host, and for harvesting the resulting fusion protein are well known and thoroughly documented in the art. Specific protocols are described, for example, in Sambrook et al. eds (1989) "*Molecular Cloning: A Laboratory Manual*," Cold Spring Harbor Press.

It is understood that the chemically coupled immunocytokines may be produced using a variety of methods well known to those skilled in the art. For example, the antibody or an antibody fragment may be chemically coupled to the cytokine using chemically reactive amino acid side chains in the antibody or antibody fragment and the cytokine. The amino acid side chains may be covalently linked, for example, via disulfide bonds, or by means of homo- or hetero-bifunctional crosslinking reagents including, for example, N-succinimidyl 3(-2-pyridyylditio)propionate, m-maleimidobenzoyl-N-hydroxysuccinate ester, m-maleimidobenzoyl-N-hydroxysulfosuccinimide ester, and 1,4-di-[3'(2'-pyridylthio) propionamido]butane, all of which are available commercially from Pierce, Rockford, Ill.

According to methods of the invention, the combination of immunocytokines with immunocytokine uptake enhancing agents is useful for enhanced stimulation of the immune system, thereby resulting in a cytotoxic response at the site of the targeted cell type, for example, tumor or other disease cells. A combination of an immunocytokine and an immunocytokine uptake enhancing agent would be expected to have no combined or synergistic anti-tumor effect in vitro since the immunocytokine alone is non-cytotoxic.

Without wishing to be bound by any particular theory, it is believed that the effects of combined therapy in vivo may include enhanced uptake of one of the agents by the action of the other resulting in either or both (1) increased chemotherapeutic cytotoxicity (if the immunocytokine increased the uptake of the chemotherapeutic immunocytokine uptake enhancing agent into tumor cells); and/or (2) increased immune stimulation (if the immunocytokine uptake enhancing agent in some way increased uptake of the immunocytokine into the tumor). With respect to mechanism (1), earlier studies have shown that it is possible to increase the uptake of radiolabeled antibodies (and presumably, small molecule drugs) into tumors by prior treatment with high doses of an antibody-IL2 immunoconjugate that induces a local vascular leak (see for example, Hornick et al., 1999, CLIN CANCER RES 5:51-60). If this particular mechanism is operative in the combination therapy of immunocytokines and immunocytokine uptake enhancing agents, it would be necessary to first treat the tumor-bearing animal with the immunocytokine. However, if a single dose of an immunocytokine uptake enhancing agent given prior to treatment with an immunocytokine resulted in a synergistic effect on anti-tumor activity, then such a mechanism could not be operative. Rather, a more likely explanation would be that treatment with an immunocytokine uptake enhancing agent increased the uptake of the immunocytokine by mechanism (2). This hypothesis could be further supported by demonstrating that co-administration with an immunocytokine uptake enhancing agent increases the uptake of a radiolabeled immunocytokine into a solid tumor.

According to methods of the invention, an advantage of the combination therapy is that the administration of an immunocytokine enhances the cytotoxic effect of a chemotherapeutic agent that acts as immunocytokine uptake enhancing agent. Therefore, a lower dosage of the chemotherapeutic agent may be administered to a patient. Accordingly, the suppression of some aspects of a patient's immune system, often associated with treatment using a chemotherapeutic agent, is reduced. In one embodiment of the invention, a single dose of chemotherapeutic immunocytokine uptake enhancing agent is administered to a patient before an immunocytokine is administered. The chemotherapeutic immunocytokine uptake enhancing agent is administered preferably between about 4 days and about 4 hours, and most preferably about 24-48 hours, before the immunocytokine. In another embodiment of the invention several doses of the chemotherapeutic immunocytokine uptake enhancing agent are administered to a patient before the immunocytokine is administered. In further embodiments of the invention, the chemotherapeutic immunocytokine uptake enhancing agent may be administered before, at the same time, and/or after the immunocytokine.

Paclitaxel is an example of a chemotherapeutic immunocytokine uptake enhancing agent that can suppress or compromise aspects of a patient's immune system. While most immune potentiating effects of paclitaxel are mediated through macrophage/monocyte cells, many studies on lymphocyte function indicate a detrimental effect of paclitaxel on this subset. For example, paclitaxel treatment was found to severely compromise the proliferative capacity of lymphocytes in both normal and tumor-bearing mice (Mullins et al., 1998, IMMUNOPHARMACOL IMMUNOTOXICOL 20:473-492), and to impair both the cytotoxicity of NK cells and the generation of lymphokine-activated cytotoxicity in cell cultures containing IL-2 (Chuang et al., 1993, GYNECOL ONCOL 49:291-298). In fact, the available evidence points to the lymphocyte subset of cells as the essential effector population in the anti-tumor activity of immunocytokines (Lode et al, 1998, PHARMACOL THER 80:277-292. Experimental evidence contained within the present invention has revealed several novel findings that would not have been predicted by the prior art, especially with respect to the order of drug administration.

Taxanes may be co-administered simultaneously with the immunocytokine, or administered separately by different routes of administration. Compositions of the present invention may be administered by any route that is compatible with the particular molecules. Thus, as appropriate, administration may be oral or parenteral, including intravenous and intraperitoneal routes of administration.

The compositions of the present invention may be provided to an animal by any suitable means, directly (e.g., locally, as by injection, implantation or topical administration to a tissue locus) or systemically (e.g., parenterally or orally). Where the composition is to be provided parenterally, such as by intravenous, subcutaneous, ophthalmic, intraperitoneal, intramuscular, buccal, rectal, vaginal, intraorbital, intracerebral, intracranial, intraspinal, intraventricular, intrathecal, intracisternal, intracapsular, intranasal or by aerosol administration, the composition preferably comprises part of an aqueous or physiologically compatible fluid suspension or solution. Thus, the carrier or vehicle is physiologically acceptable so that in addition to delivery of the desired composition to the patient, it does not otherwise adversely affect the patient's electrolyte and/or volume balance. The fluid medium for the agent thus can comprise normal physiologic saline (e.g., 9.85% aqueous NaCl, 0.15 M, pH 7-7.4). For many taxanes, the formulations are generally more complex, due to their generally unfavorable solubility properties. For example, the standard formulation for paclitaxel is 10% Cremophor, 10% ethanol, and 80% saline (0.9% NaCl), while the formulation for docetaxel is a 1:1 ethanol:polysorbate 80 solution that is diluted 1:10 into 5% glucose solution prior to administration (Bissery and Lavelle, 1999). However, other formulations including taxanes and newly synthesized analogs will be recognized and/or routinely developed by those skilled in the art.

Preferred dosages of the immunocytokine per administration are within the range of 0.1 mg/m$^2$-100 mg/m$^2$, more preferably, 1 mg/m$^2$-20 mg/m$^2$, and most preferably 2 mg/m$^2$-6 mg/m$^2$. Preferred dosages of the immunocytokine uptake enhancing agent will depend generally upon the type of immunocytokine uptake enhancing agent used, however, optimal dosages may be determined using routine experimentation. Administration of the immunocytokine and/or the immunocytokine uptake enhancing agent may be by periodic bolus injections, or by continuous intravenous or intraperitoneal administration from an external reservoir (for example, from an intravenous bag) or internal (for example, from a bioerodable implant). Furthermore, it is contemplated that the immunocytokine of the invention may also be administered to the intended recipient together with a plurality of different immunocytokine uptake enhancing agents. It is contemplated, however, that the optimal combination of immunocytokines and immunocytokine uptake enhancing agents, modes of administration, dosages may be determined by routine experimentation well within the level of skill in the art.

A variety of methods can be employed to assess the efficacy of combined therapy using antibody-cytokine fusion proteins and immunocytokine uptake enhancing agents on immune responses. For example, the animal model described in the examples below, or other suitable animal models, can be used by a skilled artisan to test which immunocytokine uptake enhancing agents, or combinations of immunocytokine uptake enhancing agents, are most effective in acting synergistically with an immunocytokine (for example, an antibody-IL2 fusion protein) to enhance the immune destruction of established tumors. The immunocytokine uptake enhancing agent, or combination of immunocytokine uptake enhancing agents, can be administered prior to, or simultaneously with, the course of immunocytokine therapy and the effect on the tumor can be conveniently monitored by volumetric measurement. Further, as novel immunocytokine uptake enhancing agents are identified, a skilled artisan will be able to use the methods described herein to assess the potential of these novel compounds to enhance or otherwise modify the anti-cancer activity of antibody-cytokine fusion proteins.

Alternatively, following therapy, tumors can be excised, sectioned and stained via standard histological methods, or via specific immuno-histological reagents in order to assess the effect of the combined therapy on the immune response. For example, simple staining with hematoxolin and eosin can reveal differences in lymphocytic infiltration into the solid tumors which is indicative of a cellular immune response. Furthermore, immunostaining of sections with antibodies to specific classes of immune cells can reveal the nature of an induced response. For example, antibodies that bind to CD45 (a general leukocyte marker), CD4 and CD8 (for T cell subclass identification), and NK1.1 (a marker on NK cells) can be used to assess the type of immune response that has been mediated by the immunocytokines of the invention.

Alternatively, the type of immune response mediated by the immunocytokines can be assessed by conventional cell subset depletion studies described, for example, in Lode et al. (1998) Blood 91: 1706-1715. Examples of depleting antibodies include those that react with T cell markers CD4 and CD8, as well as those that bind the NK markers NK1.1 and asialo GM. Briefly, these antibodies are injected to the mammal prior to initiating antibody-cytokine treatment at fairly high doses (for example, at a dose of about 0.5 mg/mouse), and are given at weekly intervals thereafter until the completion of the experiment. This technique can identify the cell-types necessary to elicit the observed immune response in the mammal.

In another approach, the cytotoxic activity of splenocytes isolated from animals having been treated with the combination therapy can be compared with those from the other treatment groups. Splenocyte cultures are prepared by mechanical mincing of recovered, sterile spleens by standard techniques found in most immunology laboratory manuals. See, for example, Coligan et al. (eds) (1988) "Current Protocols in Immunology," John Wiley & Sons, Inc. The resulting cells then are cultured in a suitable cell culture medium (for example, DMEM from GIBCO) containing serum, antibiotics and a low concentration of IL-2 (~10 U/mL). For example, in order to compare NK activity, 3 days of culture normally is optimal, whereas, in order to compare T cell cytotoxic activity, 5 days of culture normally is optimal. Cytotoxic activity can be measured by radioactively labeling tumor target cells (for example, LLC cells) with $^{51}$Cr for 30 min. Following removal of excess radiolabel, the labeled cells are mixed with varying concentrations of cultured spleen cells for 4 hr. At the end of the incubation, the $^{51}$Cr released from the cells is measured by a gamma counter which is then used to quantitate the extent of cell lysis induced by the immune cells. Traditional cytotoxic T lymphocyte (or CTL) activity is measured in this way.

The invention is illustrated further by the following non-limiting examples.

EXAMPLE 1

Animal Models

Murine cancer models were developed to study the effect of combining immunocytokines and taxanes in mediating effective cytotoxic responses against a tumor. The immunocytokines used in the following examples bind EpCAM, a human tumor antigen found on most epithelial derived tumors. (see, Perez and Walker (1989) J. Immunol. 142: 3662-3667). In order to test the efficacy in an immuno-competent murine model, it was necessary to express the human antigen on the surface of a mouse tumor cell that is syngeneic with the mouse host. Lewis lung carcinoma (LLC) cells, a well known mouse lung cancer cell line, was the first cell line selected for this purpose. This cell line is known to produce high levels of inhibitors of the immune system and to induce IL-10 production from immune cells in the tumor microenvironment leading to localized immune suppression (Sharma et al., 1999, J IMMUNOL 163:5020-5028). The human tumor antigen, EpCAM (also referred to as KSA), was expressed on the surface of LLC cells so that it could be targeted in vivo with immunocytokines derived from the mouse anti-EpCAM antibody, KS-1/4. This was accomplished by transducing the EpCAM cDNA sequence with a recombinant retroviral vector as described (Gillies, U.S. patent application Ser. No. 09/293,042) resulting in a cell line designated LLC/KSA. These cells were maintained in DMEM, supplemented with 10% heat inactivated fetal bovine serum, L-glutamine, penicillin/streptomycin and Geneticin (GIBCO) at 37° C. and 7.0% $CO_2$.

Additional cell lines representing carcinoma of different tissue origins were engineered in a similar manner. 4T1, a non-immunogenic murine mammary carcinoma cell line, was provided by Dr. Paul Sondel (Univ. of Wisconsin). This line grows slowly and progressively after subcutaneous implantation and spontaneously metastasizes to many organs even prior to surgical removal of the primary tumor. It is also possible to induce experimental metastases in the lung by intravenous injection. CT26, a murine colon carcinoma cell line, derived by intrarectal injection of N-nitroso-N-methylurethane in BALB/C mice, was provided by Dr. I. J. Fidler (MD Anderson Cancer Center, Houston, Tex.). 4T1 and CT26 cells were transfected with Ep-CAM as described (Gillies et al., 1998, J IMMUNOL 160:6195-6203). 4T1/KSA cells were maintained in RPMI, supplemented with 10% heat inactivated fetal bovine serum, L-glutamine, penicillin/streptomycin and Geneticin (GIBCO) at 37° C. and 7.0% $CO_2$. CT26/KSA cells were maintained in DMEM, supplemented with 10% heat inactivated fetal bovine serum, L-glutamine, vitamins, sodium pyruvate, non-essential amino acids, penicillin/streptomycin and Geneticin (GIBCO, Gaithersberg, Md.) at 37° C. and 7.0% $CO_2$. Geneticin was added to the transfected cells to maintain KSA expression. All of the transfected cell lines grow progressively as skin tumors (after subcutaneous injection) or as metastases (after intravenous injection) and kill the mice, despite their expression of the human EpCAM molecule (a potential foreign antigen) on their cell surface.

For tumor growth studies either LLC/KSA or CT26/KSA tumors were implanted subcutaneously on the backs of mice. For LLC/KSA studies, tumors were transplanted from several stock tumors that had been injected with a single cell suspension of $1\times10^6$ cells in 100 ul of PBS. After about two weeks, tumors were aseptically collected, passed through a sieve fitted with a 150 μm screen. Cells were then passed through a syringe and 23 gauge needle tow or three times, washed twice, and resuspended in PBS. A single cell suspension of $1\times10^6$ LLC/KSA cells in 100 ul of PBS was injected subcutaneously using a 30 ½ gauge needle on the backs of mice. For CT26/KSA studies, cells growing exponentially in culture were injected as a single cell suspension of $1\times10^6$ cells in 100 μl of PBS. After tumors had become established, about 2 weeks after implantation, dosing was initiated on Day 0. Tumors were measured with calipers in three dimensions twice weekly. Tumor volumes were calculated using the equation:

$$Volume = \frac{1}{2} \times 4/3\pi(L/2 \times W/2 \times H)$$

where L=length, W=width and H=height of the tumor. Animals were weighed and general health was monitored during the course of the study. When tumors became necrotic or if animals became moribund, the animals were euthanized by $CO_2$ asphyxiation.

Data are presented in graphic form. Graphs depict individual or average tumor volumes (+/− SEM) during and after dosing. Data are also expressed as the percent of control of average tumor volumes from treated mice relative to vehicle treated mice. Student's t test was performed on the individual tumor volumes to determine significant differences.

For experimental hepatic metastases studies, mice were anesthetized using 80 mg/kg ketamine HCL (Fort Dodge Animal Health, Fort Dodge, Iowa) and 5 mg/kg xylazine (Bayer, Shawnee Mission, Kans.). A single cell suspension of $1\times10^5$ CT26/KSA cells in 100 μl of DMEM containing 25 mM HEPES (GIBCO) was injected using a 27½ gauge needle beneath the splenic capsule over a period of 60 seconds on Day 0. After another 2 minutes the splenic vessels were cauterized with a cautery unit (Roboz, Rockville, Md.) and the spleen removed. Animals were sutured using autoclips. Three weeks after inoculation the animals were sacrificed; their livers were removed and weighed. The livers were then fixed and stained in Bouin's solution (Sigma, St. Louis Mo.).

Data are presented in graphic form. Graphs depict average tumor burdens (+/− SEM) at the time of sacrifice. Tumor burdens were determined by subtracting the weight of a normal liver from the weight of the experimental livers. Data are also expressed as the percent of control of the average tumor burden from treated mice relative to vehicle treated mice. Student's t test was performed on the individual tumor burdens to determine significant differences.

For experimental lung metastases studies, a single cell suspension of $2.5\times10^5$ 4T1/KSA cells in 100 μl of PBS was slowly injected using a 27½ gauge needle into the lateral tail vein on Day 0. About 3 weeks-after inoculation animals were sacrificed; their lungs were removed and weighed. The lungs were then fixed and stained in Bouin's solution (Sigma). Data are presented in graphic form. Graphs depict average tumor burdens (+/− SEM) at time of sacrifice. Tumor burden was determined by subtracting the weight of a normal lung from the weight of the experimental lungs. Data are also expressed as the percent of control of average tumor burden from treated mice relative to vehicle treated mice. Student's t test was performed on the individual tumor burdens to determine significant differences.

EXAMPLE 2

Preparation of Antibody-Fusion Proteins (Immunocytokines)

Several antibody-cytokine fusion proteins are discussed in the following examples.

huKS-huγ1-huIL2 (Abbreviated, KS-IL2)

A gene encoding huKS-huγ1-huIL2 fusion protein was prepared and expressed essentially as described in Gillies et al. (1998) J. Immunol. 160: 6195-6203 and U.S. Pat. No. 5,650,150. Briefly, humanized variable regions of the mouse KS1/4 antibody (Varki et al., (1984) Cancer Res. 44: 681-687) were modeled using the methods disclosed in Jones et al. (1986) Nature 321: 522-525, which involved the insertion of the CDRs of each KS1/4 variable region into the consensus framework sequences of the human variable regions with the highest degree of homology. Molecular modeling with a Silicon Graphics Indigo work station implementing BioSym software confirmed that the shapes of the CDRs were maintained. The protein sequences then were reverse translated, and genes constructed by the ligation of overlapping oligonucleotides.

The resulting variable regions were inserted into an expression vector containing the constant regions of the human κ light chain and the human Cγ1 heavy chain essentially as described in Gillies et al. (1992) Proc. Natl. Acad. Sci. USA 89: 1428-1432, except that the metallothionein promoters and immunoglobulin heavy chain enhancers were replaced by the CMV promoter/enhancer for the expression of both chains. Fusions of the mature sequences of IL-2 to the carboxy terminus of the human heavy chains were prepared as described in Gillies et al. (1992) Proc. Natl. Acad. Sci. USA 89:1428-1432, except that the 3' untranslated regions of the IL-2 gene was derived from the SV40 poly(A) region.

The IL-2 fusion protein was expressed by transfection of the resulting plasmid into NS/0 myeloma cell line with selection medium containing 0.1 μM methotrexate (MTX). Briefly, in order to obtain stably transfected clones, plasmid DNA was introduced into the mouse myeloma NS/0 cells by electroporation. NS/0 cells were grown in Dulbecco's modified Eagle's medium supplemented with 10% fetal bovine serum. About $5\times10^6$ cells were washed once with PBS and resuspended in 0.5 mL PBS. Ten μg of linearized plasmid DNA then was incubated with the cells in a Gene Pulser Cuvette (0.4 cm electrode gap, BioRad) on ice for 10 min. Electroporation was performed using a Gene Pulser (BioRad, Hercules, Calif.) with settings at 0.25 V and 500 μF. Cells were allowed to recover for 10 min. on ice, after which they were resuspended in growth medium and then plated onto two 96 well plates. Stably transfected clones were selected by growth in the presence of 100 nM methotrexate, which was introduced two days post-transfection. The cells were fed every 3 days for three more times, and MTX-resistant clones appeared in 2 to 3 weeks.

Expressing clones were identified by Fc or cytokine ELISA using the appropriate antibodies (see, for example, Gillies et al. (1989) Biotechnol. 7: 798-804). The resulting fusion protein was purified by binding, and elution from protein A Sepharose (Pharmacia), in accordance with the manufacturer's instructions.

huKS-huγ4-huIL2

A gene encoding the huKS-huγ4-huIL2 fusion protein was constructed and expressed essentially as described in U.S. Ser. No. 09/256,156, filed Feb. 24, 1999, which claims priority to U.S. Ser. No. 60/075,887, filed Feb. 25, 1998.

huγ4-huIL2 fusion protein were identified, expanded, and the fusion protein purified from culture supernatants using protein A Sepharose chromatography. The purity and integrity of the Cγ4 fusion protein was determined by SDS-polyacrylamide gel electrophoresis. IL-2 activity was measured in a T-cell proliferation assay (Gillis et al. (1978) J. Immunol. 120: 2027-2032) and was found to be identical to that of the γ1-construct.

huKS-muγ2a-muIL2

A gene encoding the huKS-muγ2a-muIL2 fusion protein was constructed by replacing the human antibody constant regions and human IL-2 of the huKS-huγ1-huIL2 fusion protein, as described above, with the corresponding murine sequences. Specifically, the human Cγ1-IL2 DNA was replaced with a murine Cγ2a cDNA fragment fused to a DNA encoding murine IL-2. Briefly, the $V_H$ region of the huKS was joined in frame to the murine γ2a cDNA by performing overlapping PCR using overlapping oligonucleotide primers:

(sense) 5' CC GTC TCC TCA *GCC AAA ACA ACA GCC CCA TCG GTC* (SEQ ID NO:1);

(antisense) 5' *GG GGC TGT TGT TTT GGC* TGA GGA GAC GGT GAC TGA CG (SEQ ID NO:2);

(sense) 5' C TTA AGC CAG ATC CAG TTG GTG CAG (SEQ ID NO:3); and (antisense) 5' CC CGG GGT CCG GGA GAA GCT CTT AGT C (SEQ ID NO:4).

Briefly, an Igγ4 version of the huKS-huγ1-huIL2 fusion protein, described above, was prepared by removing the immunoglobulin constant region Cγ1 gene fragment from the huKS-huγ1-huIL2 expression vector and replacing it with the corresponding sequence from the human Cγ4 gene. Sequences and sequence alignments of the human heavy chain constant regions Cγ1, Cγ2, Cγ3, and Cγ4 are disclosed in Huck et al. (1986) Nuc. Acids Res. 14: 1779-1789.

The swapping of the Cγ1 and Cγ4 fragments was accomplished by digesting the original Cγ1-containing plasmid DNA with Hind III and Xho I and purifying a large 7.8 kb fragment by agarose gel electrophoresis. A second plasmid DNA containing the Cγ4 gene was digested with Hind III and Nsi I and a 1.75 kb fragment was purified. A third plasmid containing the human IL-2 cDNA and SV40 polyA site, fused to the carboxyl terminus of the human Cγ1 gene, was digested with Xho I and Nsi I and the small 470 bp fragment was purified. All three fragments were ligated together in roughly equal molar amounts. The ligation product was used to transform competent E. coli and colonies were selected by growth on plates containing ampicillin. Correctly assembled recombinant plasmids were identified by restriction analyses of plasmid DNA preparations from isolated transformants and digestion with Fsp I was used to discriminate between the Cγ1 (no Fsp I) and Cγ4 (one site) gene inserts.

The final vector, containing the Cγ4-IL2 heavy chain replacement, was introduced into NS/0 mouse myeloma cells by electroporation (0.25 V and 500 μF.) and transfectants were selected by growth in medium containing methotrexate (0.1 μM). Cell clones expressing high levels of the huKS- The oligonucleotides of SEQ ID NOS: 1 and 2 were designed to hybridize to the junction of the $V_H$ domain of huKS and the constant region of murine γ2a cDNA (in italics). In the first round of PCR, there were two separate reactions. In one reaction, the $V_H$ of huKS DNA was used as the template with the oligonucleotides of SEQ ID NOS: 2 and 4. The primer of SEQ ID NO: 3 introduced an AflII (CTTAAG) restriction site upstream of the sequence encoding the mature amino terminus of huKS $V_H$ (in bold). In another reaction, murine γ2a cDNA was used as the template with the oligonucleotides SEQ ID NOS: 1 and 4. The primer of SEQ ID NO: 4 hybridized to the cDNA encoding the region around the C-terminus of γ2a and introduced a XmaI (CCCGGG) restriction site for subsequent ligation to the muIL2 cDNA. PCR products from the two reactions were mixed and subjected to a second round of PCR, using the oligonucleotides of SEQ ID NOS: 3 and 4. The resulting PCR product was cloned, and upon sequence verification, the AflII-XmaI fragment encoding the $V_H$ of huKS and the murine γ2a constant region was used for ligation to the DNA encoding the signal peptide at the AflII site and the muIL2 cDNA at the XmaI site.

The murine IL2 cDNA was cloned from mRNA of murine peripheral blood mononuclear cells using the oligonucleotides set forth in SEQ ID NOS: 5 and 6, namely:

(sense) 5' GGC CCG GGT AAA GCA CCC ACT TCA AGC TCC (SEQ ID NO.5); and (antisense) 5' CCCTCGAGTTATTGAGGGCTTGTTG (SEQ ID NO.6).

The primer of SEQ ID NO: 5 adapted the muIL2 (sequence in bold) to be joined to mu γ2a at the XmaI restriction site (CCCGGG). The primer of SEQ ID NO: 6 introduced an XhoI restriction site (CTCGAG) immediately after the translation termination codon (antisense in bold)

Similarly, the variable light ($V_L$) domain of huKS was joined to the mu κ cDNA sequence by overlapping PCR. The overlapping oligonucleotides used included .

(sense) 5' G GAA ATA AAA *CGG GCT GAT GCT GCA CCA ACT G* (SEQ ID NO.7);

(antisense) 5' *GC AGC ATC AGC CCGTT TTA TTT CCA GCT TGG TCC* (SEQ ID NO.8);

(sense) 5' C TTA AGC GAG ATC GTG CTG ACC CAG (SEQ ID NO.9); and (antisense) 5' CTC GAG CTA ACA CTC ATT CCT GTT GAA GC (SEQ ID NO.10).

The oligonucleotides were designed to hybridize to the junction of the $V_L$ of huKS and the constant region of murine κ cDNA (in italics). In the first round of PCR, there were two separate reactions. In one reaction, the $V_L$ of huKS DNA was used as template, with the oligonucleotides set forth in SEQ ID NOS. 8 and 9, which introduced an AflII (CTTAAG) restriction site upstream of the sequence encoding the mature amino terminus of huKS $V_L$ (in bold). In the other reaction, murine κ cDNA was used as template, with the oligonucleotides set forth in SEQ ID NOS. 7 and 10, which introduced an XhoI restriction site after the translation termination codon (antisense in bold).

PCR products from the two reactions were mixed and subjected to a second round of PCR using the oligonucleotide primers set forth in SEQ ID NOS. 9 and 10. The resultant PCR product was cloned, and upon sequence verification, the AflII-XhoI fragment encoding the $V_L$ of huKS and the murine κ constant region was ligated to the DNA encoding the signal peptide at the AflII site.

Both the murine heavy and light chain sequences were used to replace the human sequences in pdHL7. The resulting antibody expression vector, containing a dhfr selectable marker gene, was electroporated (6.25 V, 500 µF) into murine NS/0 myeloma cells and clones selected by culturing in medium containing 0.1 µM methotrexate. Transfected clones, resistant to methotrexate, were tested for secretion of antibody determinants by standard ELISA methods. The fusion proteins were purified via protein A Sepharose chromatography according to the manufacturers instructions.

huKS-muγ2a-muIL12

A gene encoding the huKS-muγ2a-muIL12 fusion protein was constructed and expressed essentially as described in U.S. Ser. No. 08/986,997, filed Dec. 8, 1997, and Gillies et a/. (1998) J. Immunol. 160: 6195-6203. Briefly, this was accomplished by fusing the murine p35 IL-12 subunit cDNA to the huKS-muγ2a heavy chain coding region prepared previously. The resulting vector then was transfected into an NS/0 myeloma cell line pre-transfected with, and capable of expressing p40 IL-12 subunit. In other words, a cell line was transfected with p40 alone and a stable, high expressing cell was selected, which was then used as a recipient for transfection by the p35 containing fusion protein (i.e., sequential transfection).

The murine p35 and p40 IL-12 subunits were isolated by PCR from mRNA prepared from spleen cells activated with Concanavalin A (5 µg/mL in culture medium for 3 days). The PCR primers used to isolate the p35 encoding nucleic acid sequence which also adapted the p35 cDNA as an XmaI-XhoI restriction fragment included:

5' CCCCGGGTAGGGTCATTCCAGTCTCTGG (SEQ ID NO:11); and

5' CTCGAGTCAGGCGGAGCTCAGATAGC (SEQ ID NO:12).

The PCR primer used to isolate the p40 encoding nucleic acid sequence included:

5' TCTAGACCATGTGTCCTCAGAAGCTAAC (SEQ ID NO:13); and

5' CTCGAGCTAGGATCGGACCCTGCAG (SEQ ID NO:14).

A plasmid vector (pdHL7-huKS-muγ2a-p35) was constructed as described (Gillies et al. J. Immunol. Methods 125: 191) that contained a dhfr selectable marker gene, a transcription unit encoding a humanized KS antibody light chain, and a transcription unit encoding a murine heavy chain fused to the p35 subunit of mouse IL-12. The fusion was achieved by ligation of the XmaI to XhoI fragment of the adapted p35 subunit cDNA, to a unique XmaI site at the end of the CH3 exon of the murine γ2a gene prepared previously. Both the H and L chain transcription units included a cytomegalovirus (CMV) promoter (in place of the metallothionein promoter in the original reference) at the 5' end and, a polyadenylation site at the 3' end.

A similar vector (pNC-p40) was constructed for expression of the free p40 subunit which included a selectable marker gene (neomycin resistant gene) but still used the CMV promoter for transcription. The coding region in this case included the natural leader sequence of the p40 subunit for proper trafficking to the endoplasmic reticulum and assembly with the fusion protein. Plasmid pNC-p40 was electroporated into cells, and cells were plated and selected in G418-containing medium. In this case, culture supernatants from drug-resistant clones were tested by ELISA for production of p40 subunit.

The pdHL7-huKS-muγ2a-p35 expression vector was electroporated into the NS/0 cell line already expressing murine p40, as described in Gillies et al. (1998) J. Immunol. 160: 6195-6203. Transfected clones resistant to methotrexate were tested for secretion of antibody determinants and mouse IL-12 by standard ELISA methods. The resulting protein was purified by binding to, and elution from a protein A Sepharose column in accordance with the manufacturers instructions.

EXAMPLE 3

In vitro Cytotoxic Activity of Combination Therapy

The cell lines engineered for use in animal models (example 1) were tested for their sensitivity to taxane-induced cytotoxicity in cell culture in the presence or absence of the an IL-2 based immunocytokine consisting of the humanized form of the KS-1/4 antibody fused at the carboxyl terminus of the H chain to human IL-2 (huKS-huγ1-huIL2, hereafter abbreviated, KS-IL2). Cells were seeded at 1000 cell/well in 96 well flat-bottom plates and incubated for 24 hours at 37° C., 7% $CO_2$. Paclitaxel, at 2-fold dilutions from 200 ng/ml to 3.125 ng/ml, KS-IL2, at 200 ng/ml and IL-2, at 33.3 ng/ml (the equivalent amount of IL-2 in KS-IL2) were added in duplicate to the cell culture plates and incubated for 6 days at 37° C., 7% $CO_2$. The MTS calorimetric assay (Promega), a measure of cell viability based on the cellular conversion of a tetrazolium salt, was performed directly in the 96 well plates. After plates were read and recorded, viable adherent cells were stained with Crystal violet (Sigma, St. Louis, Mo). Crystal violet stained plates were used to verify MTS assay results. Results are expressed in tabular form. The $IC_{50}$ is the concentration of drug that produced cytotoxicity at a level of 50% of control.

A cytotoxicity assay was performed with paclitaxel (3 to 200 ng/ml) alone or combined with KS-IL2 (200 ng/ml) or IL-2 (33.3 ng/ml, the equivalent amount of IL-2 in KS-IL2) against CT26/KSA, LLC/KSA and 4T1/KSA cells. There was little to no cytotoxicity of KS-IL2 or IL-2 alone on the three cell lines tested (81% to 101% of control, Table 1). The addition of either KS-IL2 or IL-2 did not affect the cytotoxicity of Paclitaxel. Therefore, since neither KS-IL2 nor IL-2 affects the cytotoxicity of paclitaxel, any enhancement in anti-tumor activity in mice by the combined treatments must be due to other mechanisms, which occur only in the tumor-bearing animal.

TABLE 1

Cytotoxicity of Paclitaxel in combination with IL-2 or KS-IL2

|  | CT26/KSA[a] | LLC/KSA[b] | 4T1/KSA[b] |
| --- | --- | --- | --- |
| Paclitaxel $IC_{50}$ (ng/ml) | | | |
| Taxol | 27 | 6 | 16 |
| Taxol + IL-2 (33 ng/ml) | 30 | 8 | 20 |
| Taxol + KS-IL2 (200 ng/ml) | 26 | 5 | 19 |
| % of Control | | | |
| IL-2 (33 ng/ml) | 97 | 100 | 95 |
| KS-IL2 (200 ng/ml) | 90 | 101 | 81 |

[a]Average of three experiments
[b]Average of two experiments

EXAMPLE 4

Combination Therapy of LLC Skin Tumors with KS-IL2 and a Taxane

Figure 2:
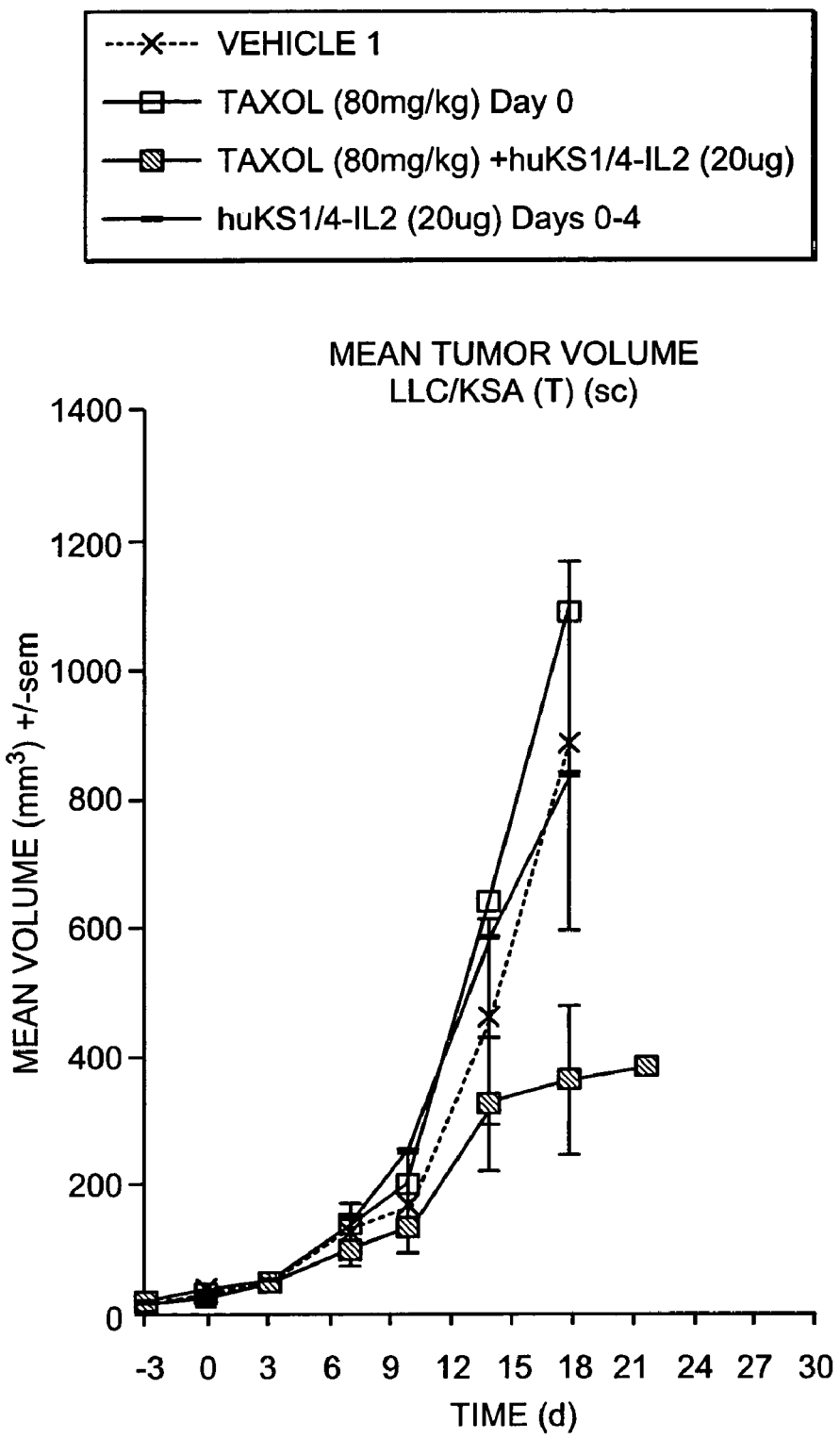
FIG. 2 shows the effect of paclitaxel and an immunocytokine on LLC/KSA tumor volume over time.

A tumor growth regression assay was performed using the aggressively growing tumor, LLC/KSA, in which a single dose of paclitaxel (80 mg/kg) was followed one week later by KS-IL2 (20 μg) administered by intravenous tail vein injection for 5 days (FIG. 2). No effect of either the paclitaxel or KS-IL2 given alone (on Days 0-4) was observed. However, when KS-IL2 was administered one week following paclitaxel, a large reduction in average tumor volume (41% of control) and a tumor growth delay (TGD) of about 8 days was observed which was significantly different than paclitaxel alone (p=0.023). No drug-related gross toxicity was observed except for a <5% weight loss in the paclitaxel treated groups.

Figure 3:
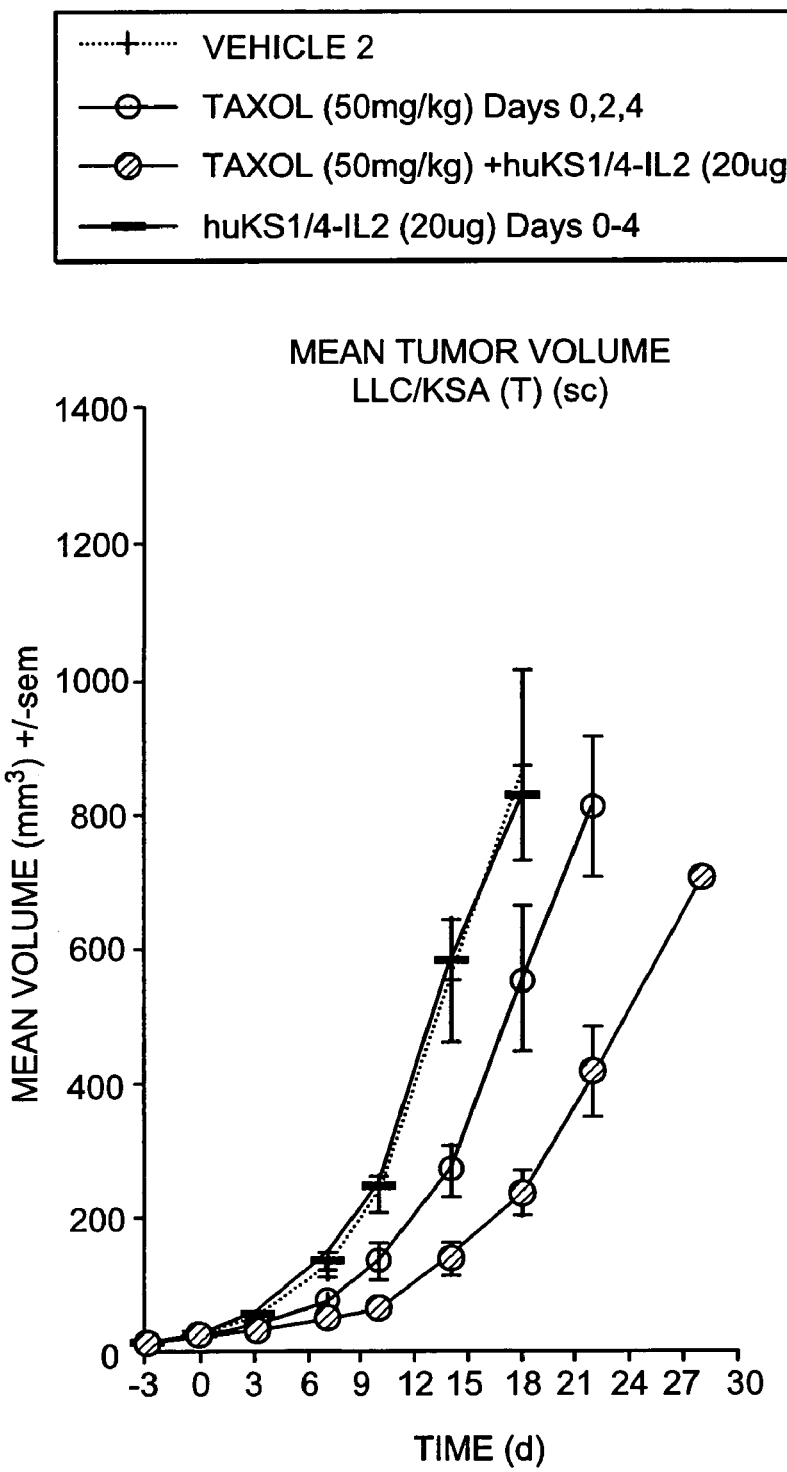
FIG. 3 shows the effect of multiple doses of paclitaxel and an immunocytokine on mean tumor volume of time.

Next, the effect of multiple doses of paclitaxel, generally considered a more effective chemotherapy schedule, was compared to a single dose of paclitaxel in combination with KS-IL2 to determine how the schedule affects the enhancement. KS-IL2 (20 μg, Days 0-4) alone again had no effect on LLC/KSA tumor growth but paclitaxel alone, when given in multiple doses (50 mg/kg, every other day), reduced the average tumor volume to 63% of control and caused a 4 day tumor growth delay (TGD) (FIG. 3). When the KS-IL2 immunocytokine was administered one week following paclitaxel treatment, a reduction in tumor volume to 27% of control and a TGD of 10 days was observed which was significantly different than paclitaxel alone (p=0.016). No drug-related gross toxicity was observed except for a <5% weight loss in the paclitaxel treated groups. The combined therapy group had even less weight loss. These positive combination therapy results are surprising considering the relatively short interval between chemotherapeutic (and potentially immune damaging) treatment and the initiation of a treatment that is based on the ability to stimulate lymphocyte proliferation and cytotoxicity.

One explanation for the combined effect is that taxane-induced apoptosis of a portion of the growing tumor mass reduced the interstitial pressure that, in turn, increased the effective uptake of KS-IL2 into the tumor. Recent studies (Griffon-Etienne et al. 1999, CANCER RES. 59:3776-3782) indicate that the effect of a single dose of paclitaxel effectively lowered interstitial fluid pressures with a maximum effect seen from 24 to 48 hours (Griffon-Etienne et al. 1999, CANCER RES. 59:3776-3782). Although this may be the best time for uptake of the immunocytokine into the tumor, it is also a very short time interval after chemotherapy. Nonetheless, we treated mice bearing LLC/KSA tumors with KS-IL2 for 5 consecutive days beginning just 24 hr after receiving a single dose of paclitaxel. Results indicate that there is an even better combined response when immunocytokine treatment was initiated earlier than a week following a single dose of paclitaxel with this tumor line as well as colon carcinoma CT26 (see below).

EXAMPLE 5

Combination Therapy of 4T1 Metastases with KS-IL2 and a Taxane

Since we found that treatment intervals between administration of a taxane and an immunocytokine could be shorter than expected, we tested combination regimens in which the taxane and the immunocytokine are given on the same day and compared a single dose (75 mg/kg) of paclitaxel with a fractionated dose (25 mg/kg×3 days) given concurrently with KS-IL2 treatment (15 μg/dose×3 days given 4 hr after paclitaxel). For this experiment we used an experimental lung metastasis model induced with 4T1/KSA breast carcinoma cells. The doses of the drugs were selected to be sub-optimal by themselves so that any potential additive or synergistic activity could be observed.

Figure 4:
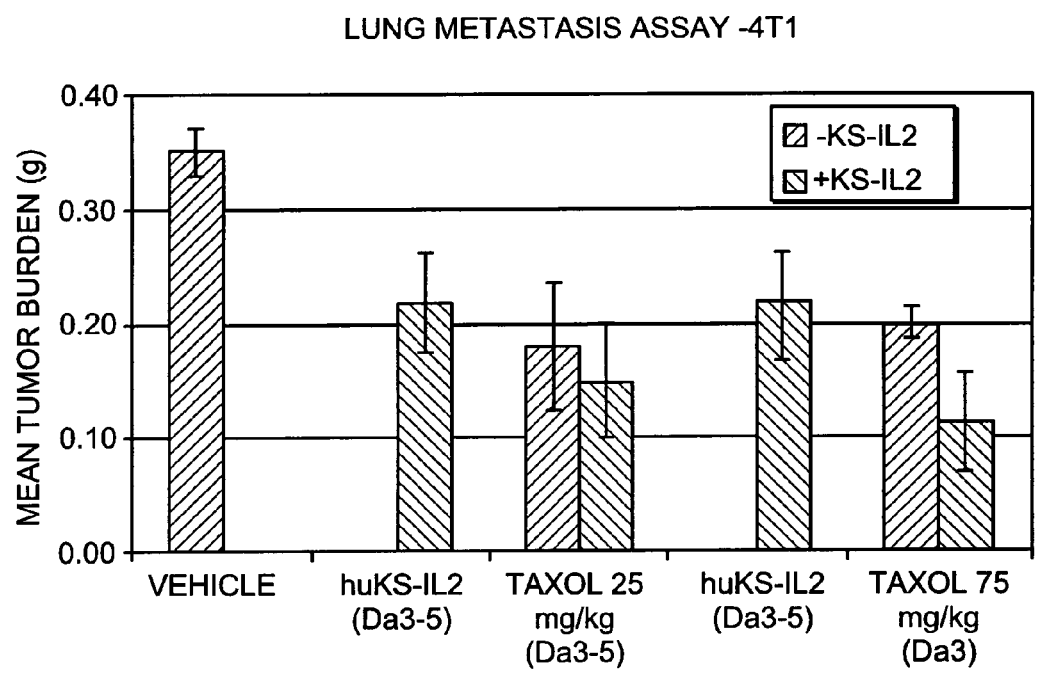
FIG. 4 shows the effect of paclitaxel and an immunocytokine on tumor weight in a lung metastasis assay.

Each agent given alone significantly (p<0.02) reduced average lung weights to a similar extent: 43% reduction for the single dose of paclitaxel, a 49% reduction for multiple doses of paclitaxel alone and a 39% reduction with KS-IL2 alone (FIG. 4). The combination of paclitaxel and KS-IL2 further reduced lung metastases slightly but was less than additive: 58% reduction for single dose paclitaxel in combination with KS-IL2 and a 68% reduction for multiple dose paclitaxel in combination with KS-IL2. Even though no synergism was observed, the single dose of paclitaxel in combination with KS-IL2 resulted in a significant difference compared to paclitaxel given alone (p=0.047).

Less than 10% weight loss was observed in all groups, however, the greatest weight loss was obtained with 25 mg/kg of paclitaxel given 3 times every other day. Based on these data, the best regimen in this 4T1 lung metastasis assay with respect to the greatest effect of combination therapy was a single dose of paclitaxel followed by KS-IL2, as was the case for the LLC/KSA tumor growth regression model. Since the dosing interval in this case was only 4 hr, the results might not have been optimal for efficient tumor uptake.

EXAMPLE 6

Combination Therapy of CT26 Skin Tumors with KS-IL2 and a Taxane

Figure 5:
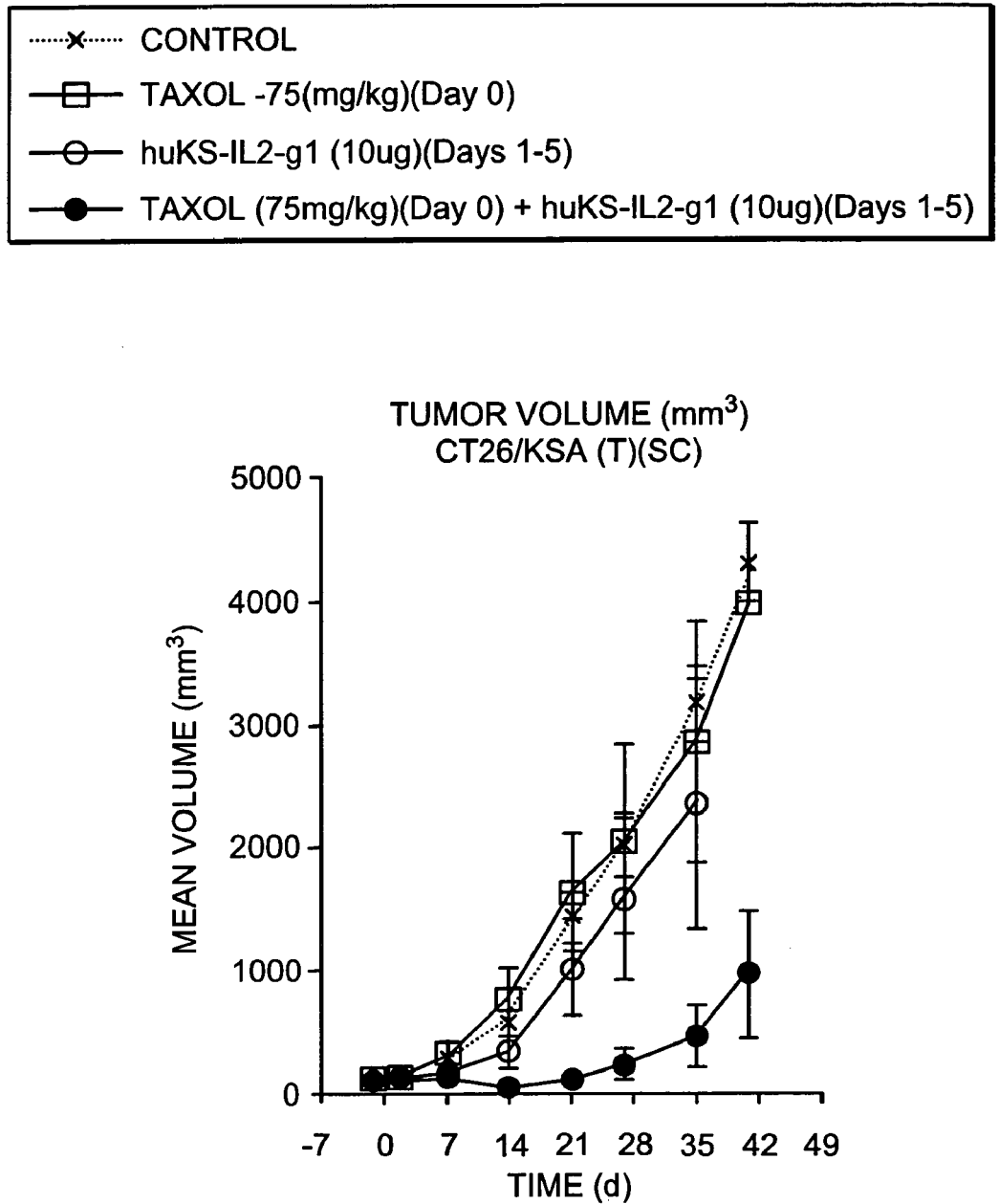
FIG. 5 shows the effect of paclitaxel and an immunocytokine on CT26/KSA tumor volume over time.

The results described in example 5 suggested that the time interval of 4 hr between dosing the two agents might be too short. Perhaps the levels of paclitaxel still remaining in the animal at the time of KS-IL2 dosing could interfere directly with lymphocyte activation, thus reducing its potential anti-tumor activity in the combination setting. Also, at the 4 hr time point, the maximum effect on the tumor interstitial pressure would not have been reached. Therefore, we designed another experiment, this time using established skin tumors of the CT26/KSA colon carcinoma, in which we combined a single dose of paclitaxel (75 mg/kg) with a 5-day course of KS-IL2 beginning 24 hr after administration of the taxane. Paclitaxel alone had no effect on tumor growth (FIG. 5). Treatment with sub-optimal doses of KS-IL2 (10 μg, Days 1-5) resulted in tumor volumes that were 71% of control. A dramatic and synergistic reduction of tumor volume to 8% of control was observed with the combination of paclitaxel and KS-IL2, which was significantly different from paclitaxel treatment alone ($p<0.001$). A minimal weight loss of ~5% was observed for both paclitaxel treated groups.

Figure 6:
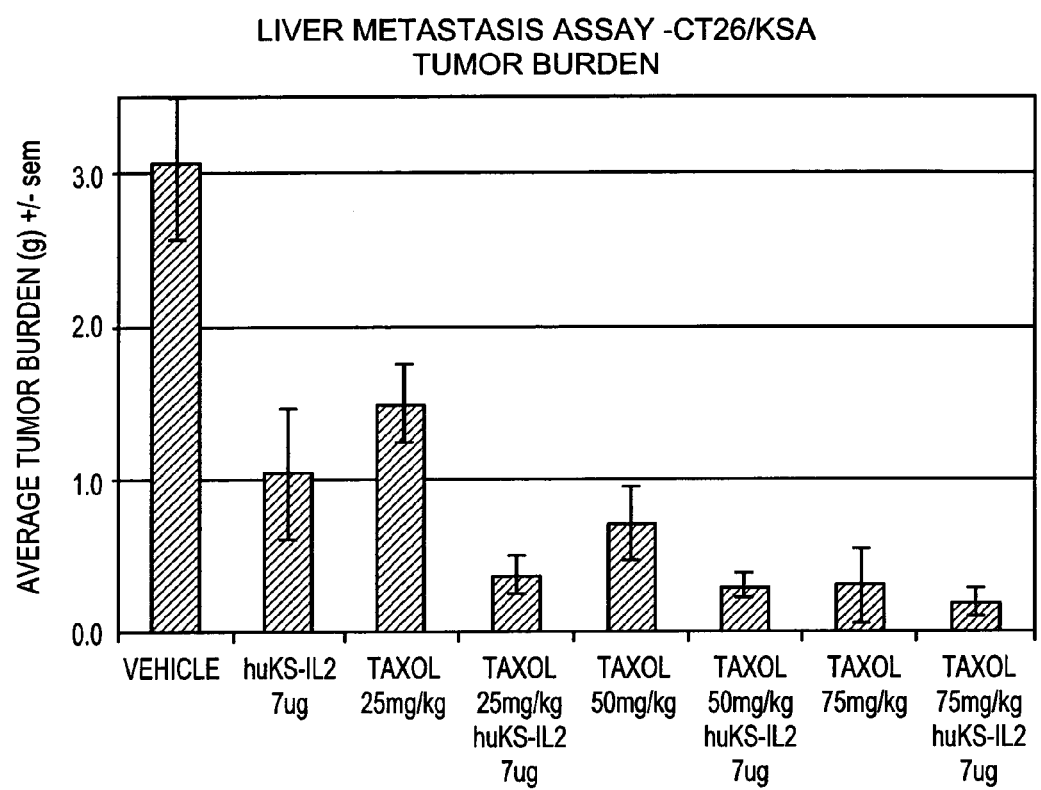
FIG. 6 shows the effect of paclitaxel and an immunocytokine on tumor weight in a liver metastasis assay.

A second experiment was performed using the CT26/KSA model, this time testing the effect of combined therapy on established liver metastases and again using the 24 hr delay between paclitaxel administration and KS-IL2 treatment. We also compared the dose response of paclitaxel in the combination therapy. Mice were injected with 25, 50, or 75 mg/kg of paclitaxel on Day 5 after metastasis induction, alone or followed one day later with KS-IL2 (7 ug) for 5 days. A dose response effect was observed for paclitaxel alone, in which 25, 50, 75 mg/kg resulted in tumor burdens of 49%, 23%, 10% of control, respectively (FIG. 6). Combining paclitaxel with KS-IL2 further reduced lung metastases to 12%, 9%, and 6% of control for the same respective doses of paclitaxel. The lowest dose of paclitaxel (25 mg/kg) in combination with KS-IL2 resulted in the greatest and most significant ($p<0.001$) reduction in tumor burden compared to the higher doses of paclitaxel with KS-IL2. Therefore, the combination of KS-IL2 preceded by paclitaxel resulted in a greater anti-tumor effect than either agent alone. Further, the lowest dose of paclitaxel in combination with KS-IL2 resulted in similar anti-tumor efficacy as the highest dose of paclitaxel alone. Hence, using a lower dose of paclitaxel in combination with KS-IL2 would reduce toxicity while maintaining good efficacy.

EXAMPLE 7

Measuring Uptake of KS-IL2 into Tumors

If the effect of single doses of cytotoxic drug treatment, prior to immunocytokine therapy, is to decrease tumor interstitial pressure and increase penetration of tumors, this should be measurable using radioactively labeled immunocytokine, e.g. KS-IL2. Purified KS-IL2 was labeled with $^{125}$I by standard procedures (reference) through contract to a commercial vendor (New England Nuclear, Billerica, Mass.). Skin tumors of CT26/KSA were implanted subcutaneously as described in Example 1 and allowed to grow until they reached from 100-200 mm$^3$. Two groups of 4 mice were injected with either paclitaxel (50 mg/kg) in vehicle or vehicle alone followed in 1 hr (Experiment 1) or 24 hr (Experiment 2) by 10 μg of $^{125}$I-KS-IL2 (95 μCi). Six hours after injecting the radiolabeled immunocytokine, the mice were sacrificed and their tumors were surgically removed. As a control, livers of the animals were also collected and all tissues were weighed and then counted in a gamma counter. Results were expressed as the counts per minute (CPM) per gram of tissue by dividing the total CPM in the tissue by the weight.

Figure 7A:
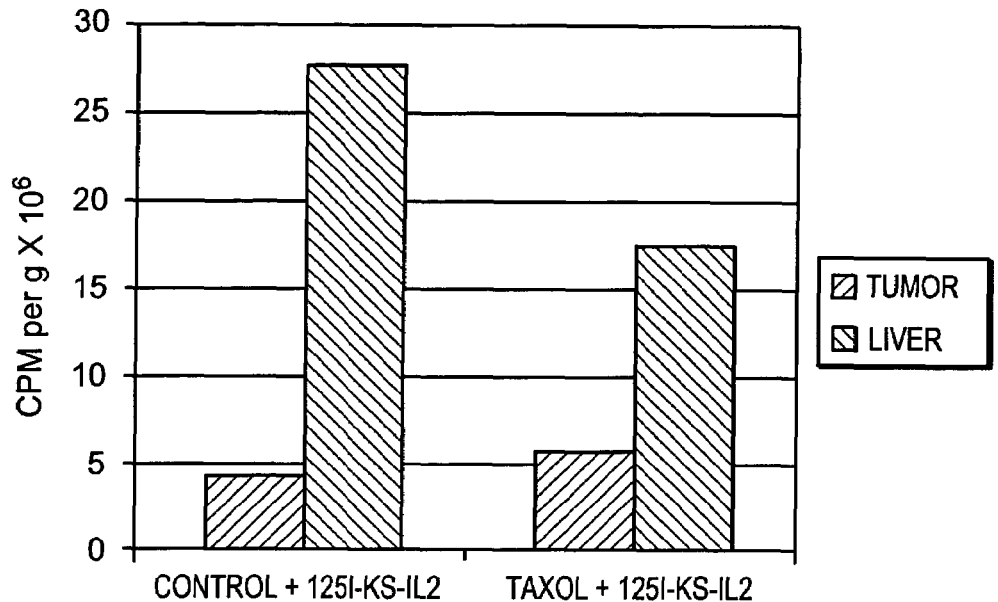
FIGS. 7A and 7B show the effect of paclitaxel on immunocytokine uptake by a tumor.
Figure 7B:
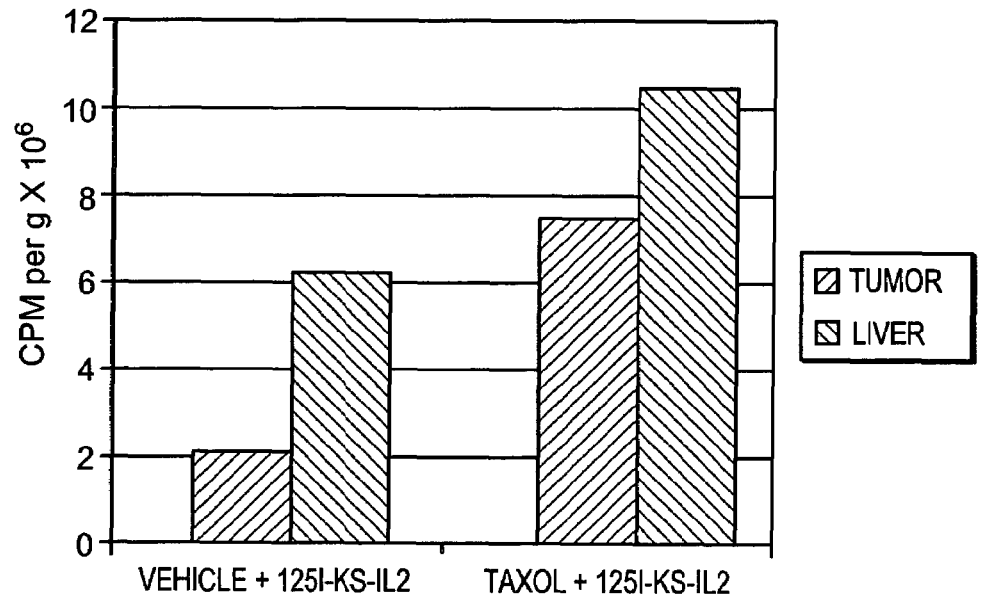

When labeled KS-IL2 was injected 1 hr after paclitaxel treatment (FIG. 7A), only a small increase in the amount of radioactivity was seen in the excised tumors from animals receiving the drug. In contrast, when labeled KS-IL2 was injected 24 hr after paclitaxel treatment, a dramatic increase in uptake was seen (>200 percent) relative to the vehicle control (FIG. 7B). This great difference in tumor uptake between the 1 hr and 24 hr time points is in agreement with the data on taxane-induced changes in interstitial pressure (Griffon-Etienne et al. 1999, CANCER RES. 59:3776-3782), and is consistent with the data in our tumor models showing that treatment beginning 24 hr after paclitaxel is more efficient than treatment at earlier times (4 hr).

Figure 8:
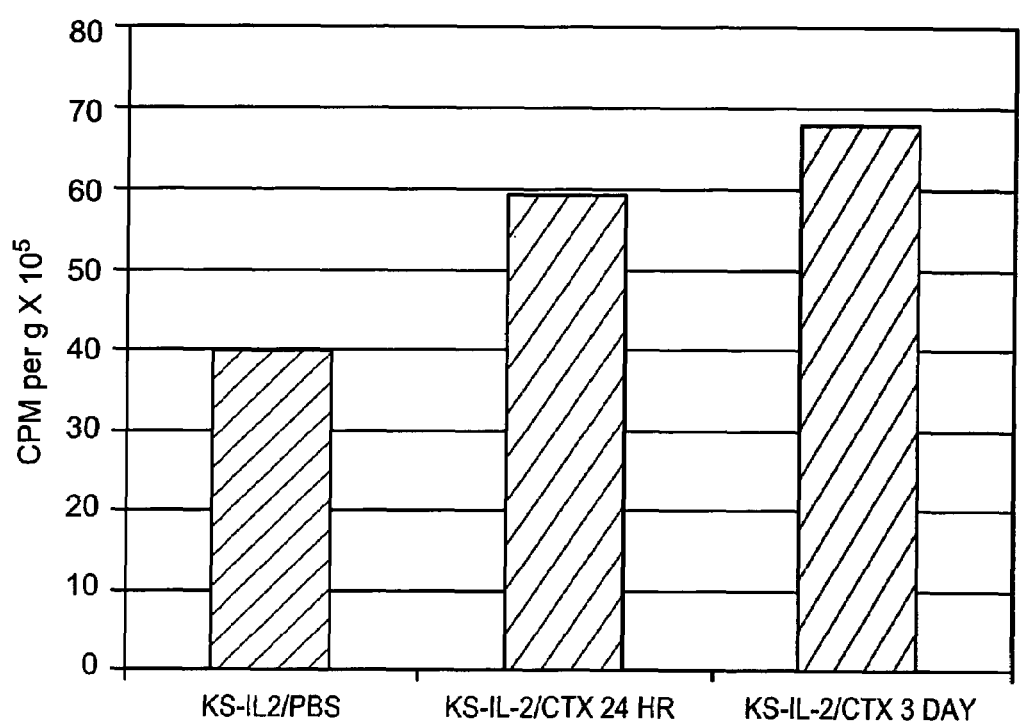
FIG. 8 shows the effect of cyclophosphamide on immunocytokine uptake by a tumor.

We also tested whether other classes of drugs could increase the uptake of labeled immunocytokine into solid tumors. In this case, mice were injected with a single dose of cyclophosphamide (40 mg/kg) either 24 hr or 3 days prior to the experiment. $^{125}$I-labeled KS-IL2 was injected into all mice, including control mice pre-treated with PBS, and the amount of radioactivity in excised tumors was determined 16 hr later. Results (FIG. 8) show that pre-treatment with cyclophosphamide increased the uptake of KS-IL2 by 48% in mice pre-treated 24 hr earlier and by 70% in mice pre-treated for 3 days.

EXAMPLE 8

Combination Therapy with huKS-huγ4-IL2 and a Taxane

New forms of immunocytokines have been described recently that have increased circulating half-lives and improved efficacy due to a reduced affinity for Fc receptors (see Gillies et. 1999, CANCER RES. 59:2159-2166). One representative of these improved IL-2 immunocytokines, huKS-huγ4-IL2, was tested in combination therapy with a single dose of paclitaxel. Again, there was improved efficacy when the two drugs were given sequentially in mice bearing CT26/KSA skin tumors.

EXAMPLE 9

Combination Therapy with huKS-muγ2a-muIL12 and a Taxane

In order to test whether the synergistic therapeutic effect is specific only for IL-2 based immunocytokines, we treated established CT26/KSA bulky tumors first with paclitaxel (single dose of 75 mg/kg) followed 24 hr later with a 5-day course of huKS-muγ2a-muIL12 (5 μg per day). This immunocytokine represents a fusion between the murine form of the HuKS antibody (i.e. the constant regions were reverted to murine C kappa and C gamma 2a) and murine IL-12. It was necessary to use murine IL-12 sequences because, unlike IL-2, this cytokine is highly species specific and the human form is not very active in the mouse. Results show that treatment with paclitaxel alone had very little effect on tumor growth. Treatment with sub-optimal doses of huKS-muγ2a-muIL12 had an anti-tumor effect and this was increased in mice that were treated first with a single dose of paclitaxel.

EXAMPLE 10

Figure 9:
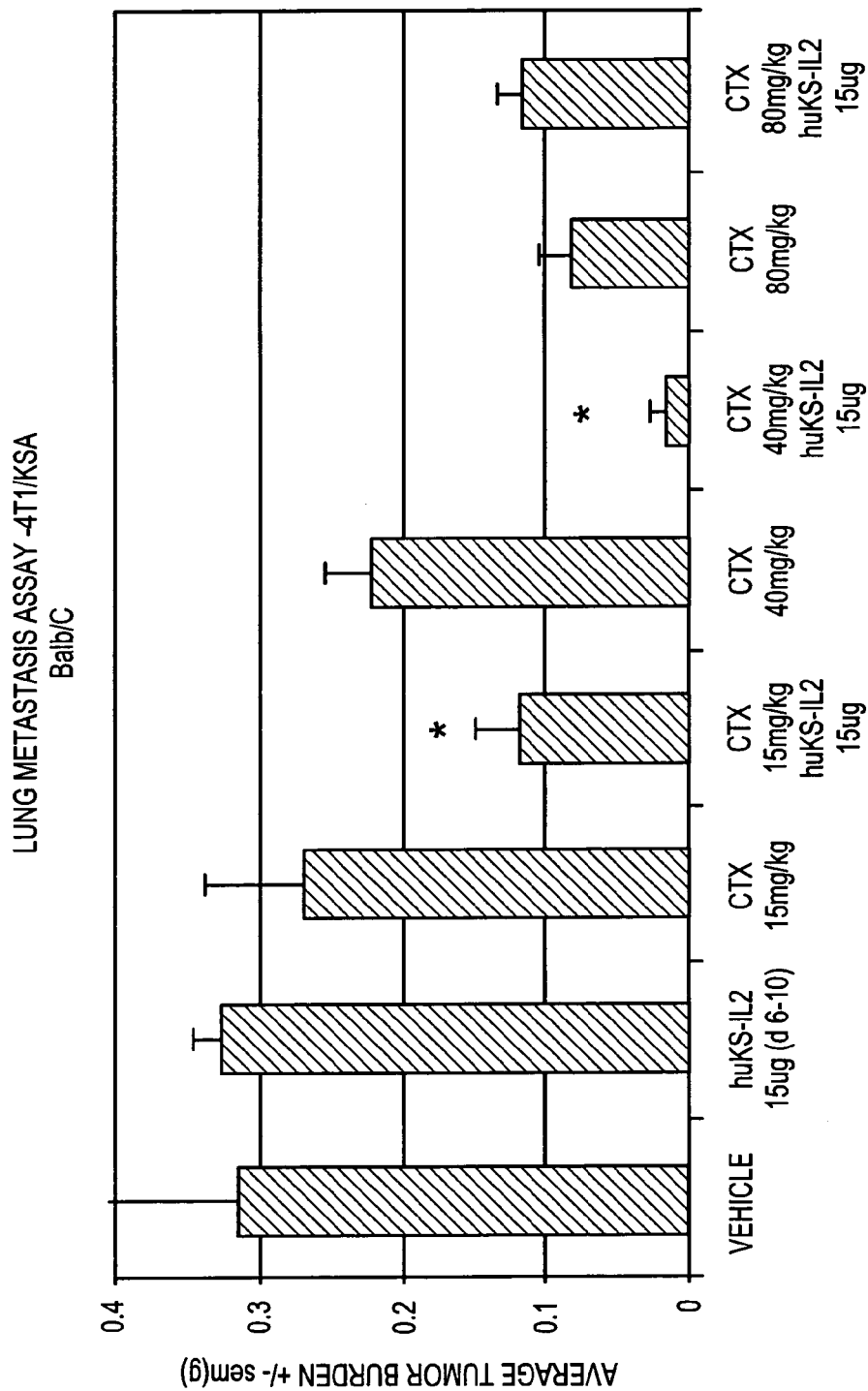
FIG. 9 shows the effect of cyclophosphamide and an immunocytokine on tumor weight in a lung metastasis assay.
Figure 9B:
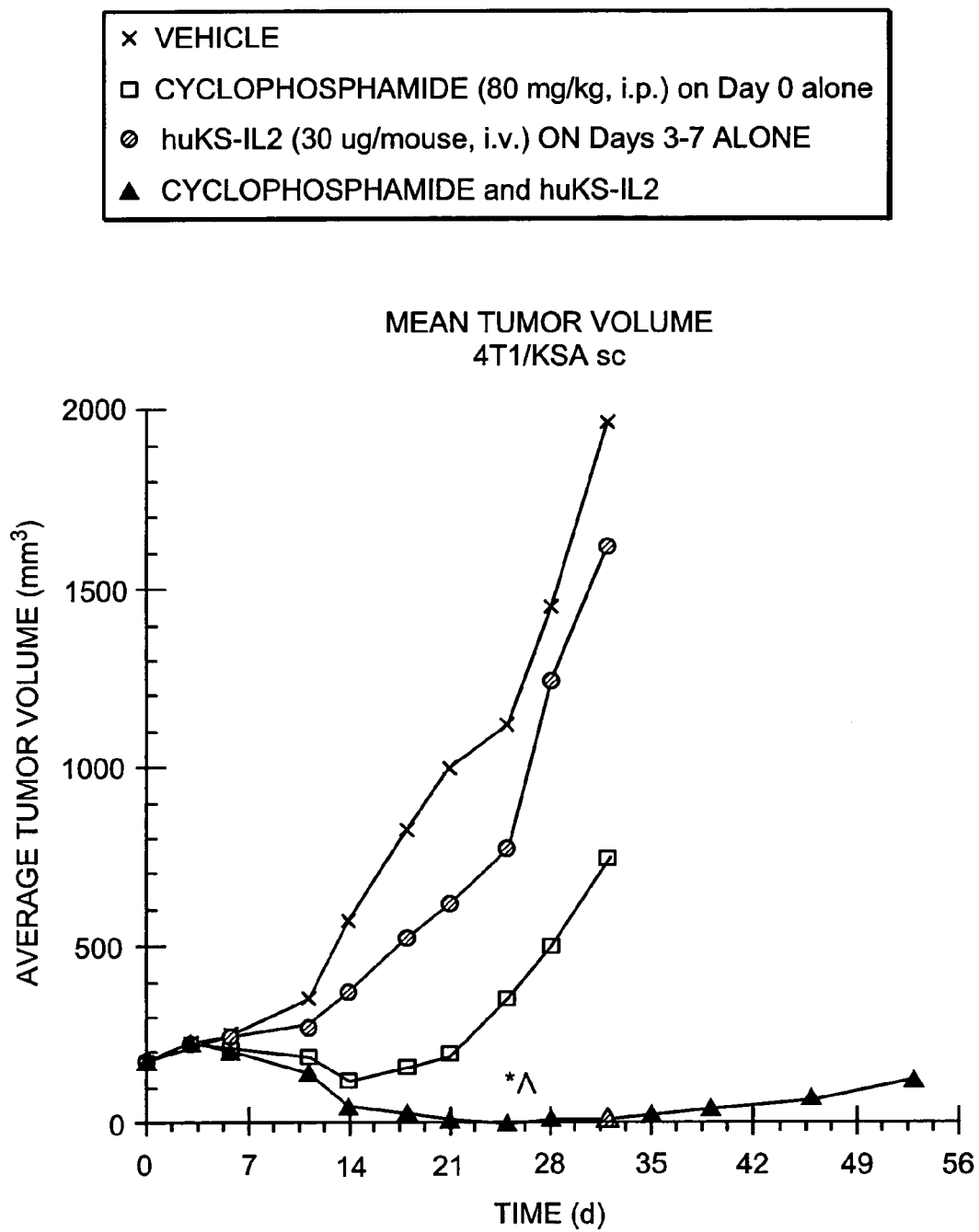
FIG. 9B shows the effect of cyclophosphamide and an immunocytokine on tumor volume in tumor growth assay.
Figure 9C:
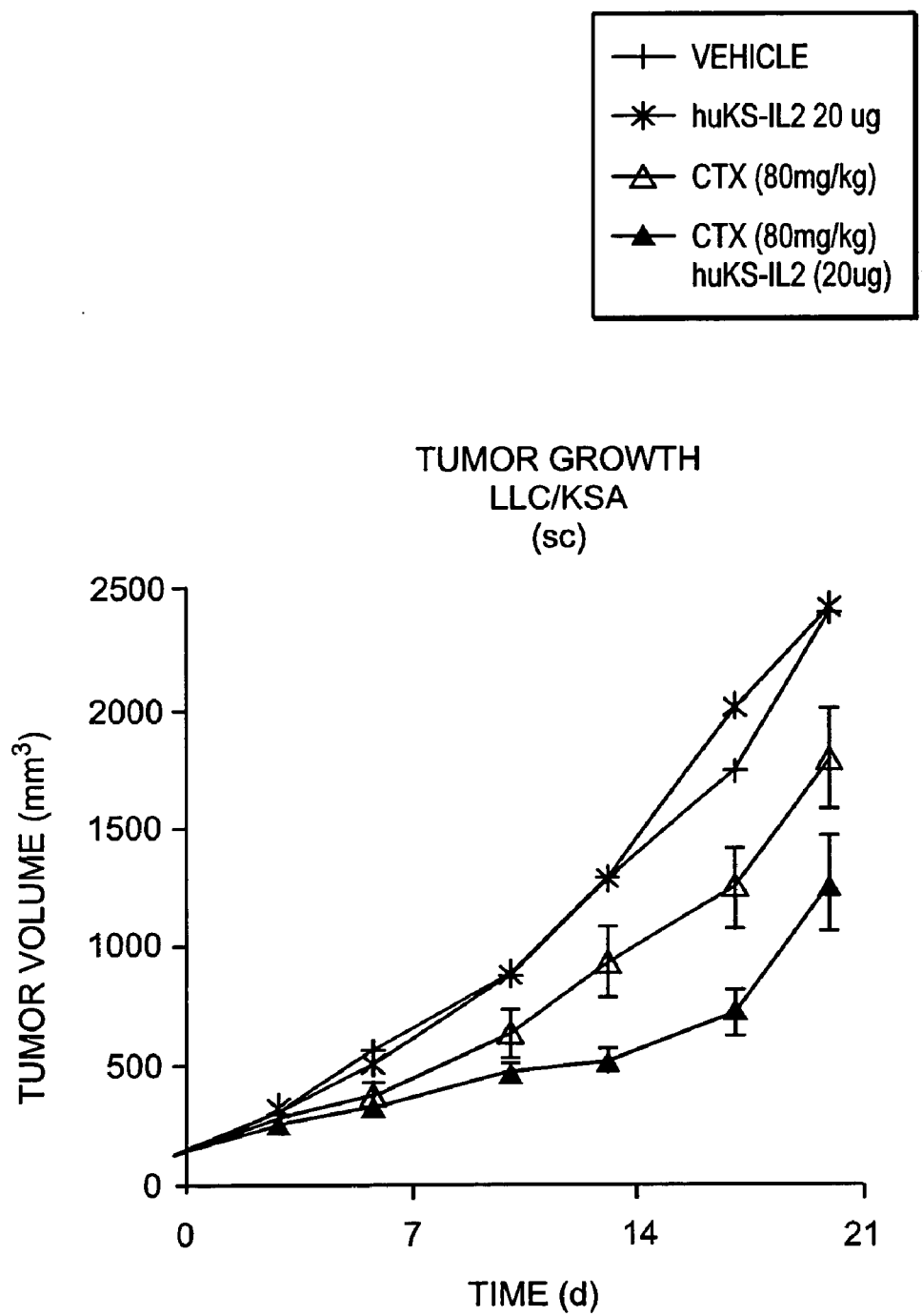
FIG. 9C shows the effect of cyclophosphamide and an immunocytokine on tumor volume in tumor growth assay.

Combination Therapy with huKS-IL2 and an Alkylating Agent i. The improved therapeutic effect of the combination of huKS-IL2 with cyclophosphamide, a chemotherapy drug in the alkylating agent class, was also demonstrated. 4T1 breast carcinoma cells were injected intravenously into immuno-competent mice to establish pulmonary metastases 3 days before treatment. Mice were treated with a single dose of cyclophosphamide (15, 40, or 80 mg/kg) followed three days later with a 5-day course of huKS-IL2 (15 ug/day). Even though the two lowest doses alone caused only a modest reduction in lung metastasis tumor burden, the combination with huKS-IL2 resulted in a significantly large decrease in tumor burden compared to cyclophosphamide alone ($p<0.05$, FIG. 9). However, at the highest dose (80 mg/kg) no synergy occurs.

ii. The improved therapeutic effect of the combination of huKS-IL2 with cyclophosphamide was also demonstrated in a tumor growth assay, in immuno-competent mice bearing established breast carcinoma subcutaneous tumors. Mice were treated with a single dose of 80 mg/kg cyclophosphamide, either alone or in combination with 5 daily doses of huKS-IL2 (30 μg) 3 days following the cyclophosphamide treatment. Average tumor volumes for huKS-IL2 and 80 mg/kg of cyclophosphamide alone were reduced by 31% and 69%, respectively (FIG. 9B). The combination treatment reduced average tumor volumes by 100% on Day 25 which was significantly different than either huKS-IL2 alone or cyclophosphamide alone ($p<0.05$) and completely eliminated tumors in six out of eight mice up to at twelve weeks after the initial treatment. Animals tolerated these treatments well with less than 10% weight loss observed in all groups.

iii. The improved therapeutic effect of the combination of huKS-IL2 with cyclophosphamide was also demonstrated in a tumor growth assay, in immuno-competent mice bearing established lung carcinoma subcutaneous tumors. Mice were treated with a single dose of 80 mg/kg cyclophosphamide, either alone or in combination with 5 daily doses of huKS-IL2 (20 μg) 3 days following the cyclophosphamide treatment. Average tumor volumes for huKS-IL2 and 80 mg/kg of cyclophosphamide alone were reduced by 2% and 27%, respectively (FIG. 9C). The combination treatment reduced average tumor volumes by 48% on Day 20 which was significantly different than either huKS-IL2 alone or cyclophosphamide alone ($p<0.05$). Animals tolerated these treatments well with less than 10% weight loss observed in all groups.

EXAMPLE 11

Combination Therapy with huKS-IL2 and an Alkylating Agent

Figure 10:
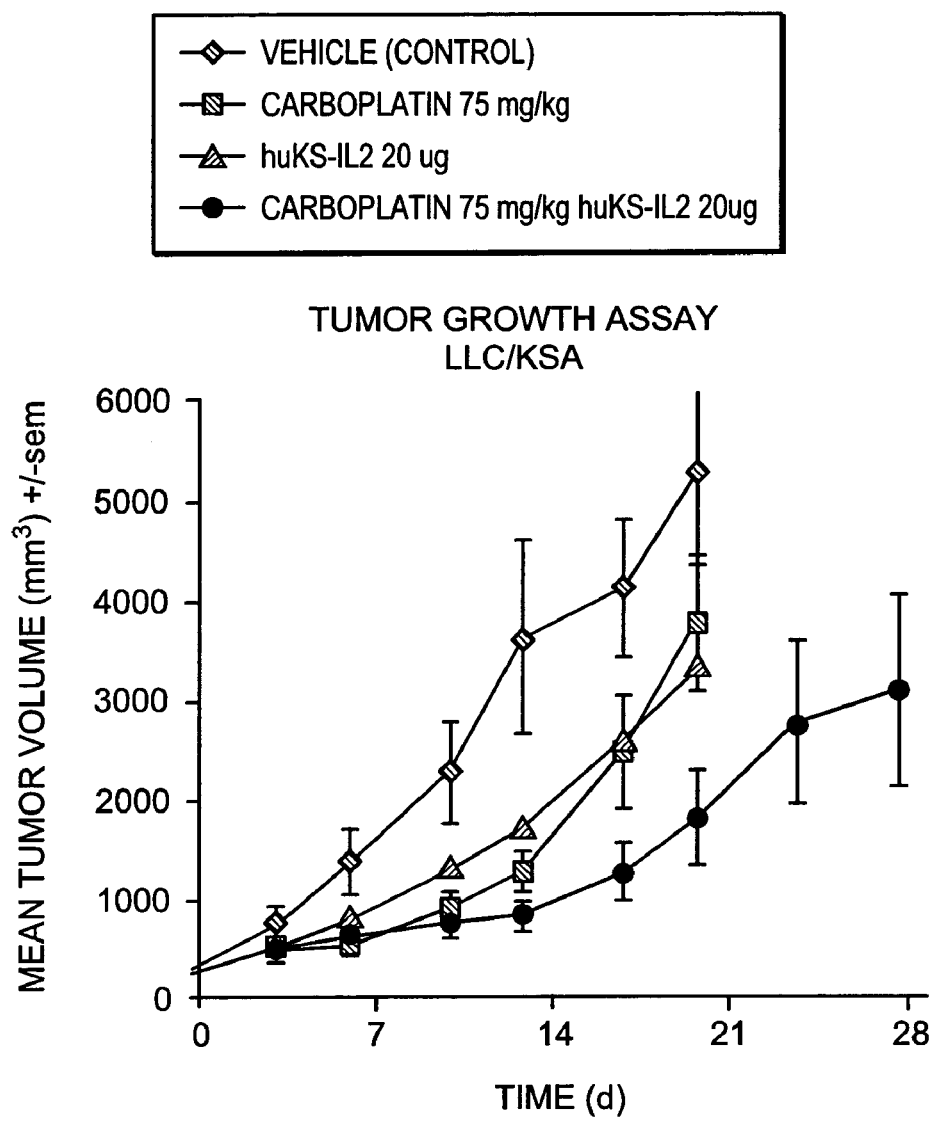
FIG. 10 shows the effect of carboplatin and an immunocytokine on tumor volume in a tumor growth assay.

The improved therapeutic effect of the combination of huKS-IL2 with Carboplatin, another chemotherapy agent in the alkylating agent class, was demonstrated. Mice bearing established non-small cell lung carcinoma subcutaneous tumors (LLC/KSA) were treated with Carboplatin (75 mg/kg) on Day 0 followed by three days later with a 5-day course of KS-IL2 (20 ug per day). Carboplatin and KS-IL2 treatment alone each resulted in a modest decrease in tumor growth, however, only the combination treatment significantly reduced the average tumor volume on Day 20 ($p<0.05$, FIG. 10). Further, the growth of tumors in which mice were treated with the combination compared to Carboplatin treatment alone was significantly different ($p<0.05$).

The invention may be embodied in other specific forms without departing from the spirit or essential characteristics thereof. The foregoing embodiments are therefore to be considered in all respects illustrative rather then limiting on the invention described herein. Scope of the invention is thus indicated by the appended claims rather than by the foregoing description, and all changes which come within the meaning and range of equivalency of the claims are intended to be embraced therein.

Each of the patent documents and scientific publications disclosed hereinabove is incorporated by reference herein.

What is claimed is:

1. A method of enhancing the immune destruction of a tumor in a mammal, the method comprising the steps of:
pre-treating a mammal with a cytotoxic agent; and
administering an immunocytokine comprising an antibody binding site and interleukin-2 wherein the pre-treating step enhances the immune destruction of the tumor.

2. The method of claim 1, wherein the antibody binding site binds to a cancer cell.

3. The method of claim 1, wherein the antibody binding site binds to a tumor specific antigen.

4. The method of claim 1, wherein the antibody binding site comprises, in an amino-terminal to carboxy-terminal direction, an immunoglobulin variable region and a CH2 domain.

5. The method of claim 4, wherein the antibody binding site further comprises a CH3 domain attached to the carboxy terminal end of the CH2 domain.

6. The method of claim 1, wherein the immunocytokine is a fusion protein comprising, in an amino-terminal to carboxy-terminal direction, (i) the antibody binding site comprising an immunoglobulin variable region capable of binding a cell surface antigen on a preselected cell type, an immunoglobulin CH1 domain, an immunoglobulin CH2 domain, and (ii) interleukin-2.

7. The method of claim 6, wherein the antibody binding site further comprises a CH3 domain interposed between the CH2 domain and interleukin-2.

8. The method of claim 1, wherein said cytotoxic agent is a taxane.

9. The method of claim 8, wherein said taxane is selected from the group consisting of paclitaxel, docetaxel and 10-deacetyl Baccatin III.

10. The method of claim 1, wherein said cytotoxic agent is an alkylating chemotherapeutic agent.

11. The method of claim 10, wherein said alkylating chemotherapeutic agent is selected from the group consisting of cyclophosphamide and carboplatin.

12. The method of claim 1, wherein two or more different cytotoxic agents are administered to said mammal.

13. The method of claim 1, wherein two or more different immunocytokines are administered to said mammal.

14. The method of claim 1, wherein the mammal is pre-treated with the cytotoxic agent for between about 4 hours and about 72 hours.

15. The method of claim 14, wherein the mammal is pre-treated with the cytotoxic agent for about 24 hours.

16. The method of claim 14, wherein the mammal is pre-treated with the cytotoxic agent for 72 hours.

17. The method of claim 1, wherein the cytotoxic agent enhances a T-cell immune response.

* * * * *

SEQUENCE LISTING

```
<160> NUMBER OF SEQ ID NOS: 15

<210> SEQ ID NO 1
<211> LENGTH: 35
<212> TYPE: DNA
<213> ORGANISM: Artificial Sequence
<220> FEATURE:
<223> OTHER INFORMATION: sense primer for junction of the huKS-mouse
      gamma 2a cDNA

<400> SEQUENCE: 1
ccgtctcctc agccaaaaca acagccccat cggtc                              35

<210> SEQ ID NO 2
<211> LENGTH: 37
<212> TYPE: DNA
<213> ORGANISM: Artificial Sequence
<220> FEATURE:
<223> OTHER INFORMATION: antisense primer for huKS-gamma 2a cDNA

<400> SEQUENCE: 2
ggggctgttg ttttggctga ggagacggtg actgacg                            37
```

<210> SEQ ID NO 3
<211> LENGTH: 25
<212> TYPE: DNA
<213> ORGANISM: Artificial Sequence
<220> FEATURE:
<223> OTHER INFORMATION: sense primer including an AflII site

<400> SEQUENCE: 3
cttaagccag atccagttgg tgcag                                         25

<210> SEQ ID NO 4
<211> LENGTH: 27
<212> TYPE: DNA
<213> ORGANISM: Artificial Sequence
<220> FEATURE:
<223> OTHER INFORMATION: antisense primer including an XmaI site

<400> SEQUENCE: 4
cccggggtcc gggagaagct cttagtc                                       27

<210> SEQ ID NO 5
<211> LENGTH: 30
<212> TYPE: DNA
<213> ORGANISM: Artificial Sequence
<220> FEATURE:
<223> OTHER INFORMATION: sense primer

<400> SEQUENCE: 5
ggcccgggta aagcacccac ttcaagctcc                                    30

<210> SEQ ID NO 6
<211> LENGTH: 25
<212> TYPE: DNA
<213> ORGANISM: Artificial Sequence
<220> FEATURE:
<223> OTHER INFORMATION: antisense primer

<400> SEQUENCE: 6
ccctcgagtt attgagggct tgttg                                         25

<210> SEQ ID NO 7
<211> LENGTH: 32
<212> TYPE: DNA
<213> ORGANISM: Artificial Sequence
<220> FEATURE:
<223> OTHER INFORMATION: sense primer

<400> SEQUENCE: 7
ggaaataaaa cgggctgatg ctgcaccaac tg                                 32

<210> SEQ ID NO 8
<211> LENGTH: 34
<212> TYPE: DNA
<213> ORGANISM: Artificial Sequence
<220> FEATURE:
<223> OTHER INFORMATION: antisense primer

<400> SEQUENCE: 8
gcagcatcag cccgttttat ttccagcttg gtcc                               34

<210> SEQ ID NO 9
<211> LENGTH: 25
<212> TYPE: DNA
<213> ORGANISM: Artificial Sequence
<220> FEATURE:
<223> OTHER INFORMATION: sense primer

<400> SEQUENCE: 9
cttaagcgag atcgtgctga cccag                                   25

<210> SEQ ID NO 10
<211> LENGTH: 29
<212> TYPE: DNA
<213> ORGANISM: Artificial Sequence
<220> FEATURE:
<223> OTHER INFORMATION: antisense primer

<400> SEQUENCE: 10
ctcgagctaa cactcattcc tgttgaagc                               29

<210> SEQ ID NO 11
<211> LENGTH: 28
<212> TYPE: DNA
<213> ORGANISM: Artificial Sequence
<220> FEATURE:
<223> OTHER INFORMATION: p35 PCR primer

<400> SEQUENCE: 11
ccccgggtag ggtcattcca gtctctgg                                28

<210> SEQ ID NO 12
<211> LENGTH: 26
<212> TYPE: DNA
<213> ORGANISM: Artificial Sequence
<220> FEATURE:
<223> OTHER INFORMATION: p35 PCR primer

<400> SEQUENCE: 12
ctcgagtcag gcggagctca gatagc                                  26

<210> SEQ ID NO 13
<211> LENGTH: 28
<212> TYPE: DNA
<213> ORGANISM: Artificial Sequence
<220> FEATURE:
<223> OTHER INFORMATION: p40 PCR primer

<400> SEQUENCE: 13
tctagaccat gtgtcctcag aagctaac                                28

<210> SEQ ID NO 14
<211> LENGTH: 25
<212> TYPE: DNA
<213> ORGANISM: Artificial Sequence
<220> FEATURE:
<223> OTHER INFORMATION: p40 PCR primer

<400> SEQUENCE: 14
ctcgagctag gatcggaccc tgcag                                   25

<210> SEQ ID NO 15
<211> LENGTH: 15
<212> TYPE: PRT
<213> ORGANISM: Artificial Sequence
<220> FEATURE:
<223> OTHER INFORMATION: Peptide linker

<400> SEQUENCE: 15

Gly Gly Gly Gly Ser Gly Gly Gly Gly Ser Gly Gly Gly Gly Ser
1               5                   10                  15